(12) United States Patent
Ziegler et al.

(10) Patent No.: US 9,033,867 B2
(45) Date of Patent: *May 19, 2015

(54) SELF-PROPELLABLE ENDOSCOPIC APPARATUS AND METHOD

(75) Inventors: Troy J. Ziegler, Plymouth, MN (US); Timothy P. Sheridan, Eagan, MN (US); William T. Ryder, Victoria, MN (US)

(73) Assignee: FUJIFILM Corporation, Tokyo (JP)

(*) Notice: Subject to any disclaimer, the term of this patent is extended or adjusted under 35 U.S.C. 154(b) by 1479 days.

This patent is subject to a terminal disclaimer.

(21) Appl. No.: 11/825,528

(22) Filed: Jul. 5, 2007

(65) Prior Publication Data

US 2008/0045790 A1    Feb. 21, 2008

Related U.S. Application Data

(63) Continuation of application No. 11/260,342, filed on Oct. 27, 2005, now Pat. No. 7,736,300, which is a continuation-in-part of application No. 10/823,141, filed on Apr. 13, 2004, now Pat. No. 6,971,990.

(60) Provisional application No. 60/462,787, filed on Apr. 14, 2003.

(51) Int. Cl.
*A61B 1/00* (2006.01)
*A61B 1/04* (2006.01)
(Continued)

(52) U.S. Cl.
CPC ............. *A61B 1/04* (2013.01); *A61B 1/00156* (2013.01); *A61B 17/3403* (2013.01);
(Continued)

(58) Field of Classification Search
USPC ............. 600/104, 106, 114–116, 101, 107, 600/121–125, 127, 129; 604/95.01–95.05, 604/264, 271; 606/1
See application file for complete search history.

(56) References Cited

U.S. PATENT DOCUMENTS 4,117,847 A    10/1978  Clayton
4,207,872 A     6/1980  Meiri et al.
(Continued)

FOREIGN PATENT DOCUMENTS

DE    10012560       9/2001
JP    55-045427 A    3/1980
(Continued)

OTHER PUBLICATIONS

"U.S. Appl. No. 11/260,342, Non Final Office Action mailed Oct. 26, 2009", 11 pgs.
(Continued)

*Primary Examiner* — Ryan Henderson
(74) *Attorney, Agent, or Firm* — Sughrue Mion, PLLC

(57) ABSTRACT

A self propelled, endoscopic apparatus formed of a flexible, fluid-filled toroid and a motorized or powerable frame The apparatus may be used to advance a variety of accessory devices into generally tubular spaces and environments for medical and non-medical applications. The apparatus when inserted into a tubular space or environment, such as the colon of a patient undergoing a colonoscopy, is advanced by the motion of the toroid. The toroid's surface circulates around itself in a continuous motion from inside its central cavity along its central axis to the outside where its surface travels in the opposite direction until it again rotates into its central cavity. As the device advances within the varying sizes, shapes and contours of body lumens, the toroid compresses and expands to accommodate and navigate the environment. The motion of the toroid can be powered or unpowered and the direction and speed may be controlled. The apparatus may be used to transport a variety of accessory devices to desired locations within tubular spaces and environments where medical and non-medical procedures may be performed.

18 Claims, 25 Drawing Sheets

(51) Int. Cl.

| | | |
|---|---|---|
| A61M 31/00 | (2006.01) | |
| A61M 37/00 | (2006.01) | |
| A61M 5/00 | (2006.01) | |
| A61M 5/14 | (2006.01) | |
| A61B 17/34 | (2006.01) | |
| A61M 25/01 | (2006.01) | |
| G02B 23/24 | (2006.01) | |
| A61B 17/00 | (2006.01) | |

(52) U.S. Cl.
CPC .. *A61B 17/3476* (2013.01); *A61B 2017/00398* (2013.01); *A61B 2017/3435* (2013.01); *A61B 2017/3488* (2013.01); *A61M 25/0116* (2013.01); *G02B 23/2476* (2013.01)

(56) References Cited

U.S. PATENT DOCUMENTS

| | | |
|---|---|---|
| 4,305,386 A | 12/1981 | Tawara |
| 4,368,739 A | 1/1983 | Nelson, Jr. et al. |
| 4,558,971 A | 12/1985 | David |
| 4,561,427 A | 12/1985 | Takada |
| 4,600,939 A | 7/1986 | Sluyter et al. |
| 4,776,845 A | 10/1988 | Davis |
| 4,866,516 A | 9/1989 | Hibino et al. |
| 4,874,364 A | 10/1989 | Morris et al. |
| 5,331,975 A | 7/1994 | Bonutti |
| 5,419,312 A | 5/1995 | Arenberg et al. |
| 5,429,609 A | 7/1995 | Yoon |
| 5,441,486 A | 8/1995 | Yoon |
| 5,562,601 A | 10/1996 | Takada |
| 5,571,114 A | 11/1996 | Devanaboyina |
| 5,575,754 A | 11/1996 | Konomura |
| 5,595,565 A | 1/1997 | Treat et al. |
| 5,620,408 A | 4/1997 | Vennes et al. |
| 5,662,587 A | 9/1997 | Grundfest et al. |
| 5,702,418 A | 12/1997 | Ravenscroft |
| 5,782,817 A | 7/1998 | Franzel et al. |
| 5,865,802 A | 2/1999 | Yoon et al. |
| 5,951,466 A | 9/1999 | Segermark et al. |
| 6,038,488 A | 3/2000 | Barnes et al. |
| 6,071,233 A | 6/2000 | Ishikawa et al. |
| 6,071,234 A | 6/2000 | Takada |
| 6,077,219 A | 6/2000 | Viebach et al. |
| 6,086,603 A | 7/2000 | Termin et al. |
| 6,162,171 A | 12/2000 | Ng et al. |
| 6,171,316 B1 | 1/2001 | Kovac et al. |
| 6,224,544 B1 | 5/2001 | Takada |
| 6,240,312 B1 | 5/2001 | Alfano et al. |
| 6,315,713 B1 | 11/2001 | Takada |
| 6,321,121 B1 | 11/2001 | Zelickson et al. |
| 6,358,199 B1 * | 3/2002 | Pauker et al. ................. 600/114 |
| 6,409,727 B1 | 6/2002 | Bales et al. |
| 6,436,107 B1 | 8/2002 | Wang et al. |
| 6,450,949 B1 | 9/2002 | Farkas et al. |
| 6,461,294 B1 | 10/2002 | Oneda et al. |
| 6,461,295 B2 | 10/2002 | Takada |
| 6,463,361 B1 | 10/2002 | Wang et al. |
| 6,508,188 B2 | 1/2003 | Dong et al. |
| 6,517,477 B1 | 2/2003 | Wendlandt |
| 6,522,906 B1 | 2/2003 | Salisbury, Jr. et al. |
| 6,537,206 B2 | 3/2003 | Takada |
| 6,604,004 B1 | 8/2003 | Zelickson et al. |
| 6,648,814 B2 | 11/2003 | Kim et al. |
| 6,663,598 B1 | 12/2003 | Carrillo, Jr. et al. |
| 6,695,771 B2 | 2/2004 | Takada |
| 6,699,179 B2 | 3/2004 | Wendlandt |
| 6,702,735 B2 | 3/2004 | Kelly |
| 6,761,717 B2 | 7/2004 | Bales et al. |
| 6,764,441 B2 | 7/2004 | Chiel et al. |
| 6,824,510 B2 | 11/2004 | Kim et al. |
| 6,866,626 B2 | 3/2005 | Long et al. |
| 6,971,990 B2 | 12/2005 | Ziegler et al. |
| 7,044,245 B2 | 5/2006 | Anhalt et al. |
| 7,087,011 B2 | 8/2006 | Cabiri et al. |
| 7,235,046 B2 | 6/2007 | Anhalt et al. |
| 7,736,300 B2 | 6/2010 | Ziegler et al. |
| 2001/0008952 A1 | 7/2001 | Takada |
| 2002/0049365 A1 | 4/2002 | Takada |
| 2002/0107478 A1 | 8/2002 | Wendlandt |
| 2002/0117097 A1 | 8/2002 | Dong et al. |
| 2002/0143237 A1 | 10/2002 | Oneda et al. |
| 2002/0156347 A1 | 10/2002 | Kim et al. |
| 2003/0060680 A1 | 3/2003 | Wendlandt |
| 2003/0065250 A1 | 4/2003 | Chiel et al. |
| 2003/0088152 A1 | 5/2003 | Takada |
| 2003/0114803 A1 * | 6/2003 | Lerner ........................... 604/276 |
| 2003/0153866 A1 | 8/2003 | Long et al. |
| 2003/0214579 A1 | 11/2003 | Iddan |
| 2003/0225433 A1 | 12/2003 | Nakao |
| 2004/0106976 A1 | 6/2004 | Bailey et al. |
| 2004/0138689 A1 | 7/2004 | Bonutti |
| 2004/0204702 A1 | 10/2004 | Ziegler et al. |
| 2004/0243144 A1 | 12/2004 | Bonadio et al. |
| 2005/0154278 A1 | 7/2005 | Cabiri et al. |
| 2006/0089533 A1 | 4/2006 | Ziegler et al. |
| 2006/0241346 A1 | 10/2006 | Takada |
| 2006/0261771 A1 | 11/2006 | Anhalt et al. |
| 2006/0264707 A1 | 11/2006 | Kinney |
| 2006/0270901 A1 | 11/2006 | Bern |
| 2007/0197868 A1 | 8/2007 | Takada |
| 2010/0198011 A1 | 8/2010 | Ziegler et al. |

FOREIGN PATENT DOCUMENTS

| | | | |
|---|---|---|---|
| JP | 58-041523 A | 3/1983 | |
| JP | 59-125540 A | 7/1984 | |
| JP | 60-030201 U | 3/1985 | |
| JP | 61-137538 A | 6/1986 | |
| JP | 01-227737 A | 9/1989 | |
| JP | 8-010102 A | 1/1996 | |
| JP | 8038416 | 2/1996 | |
| JP | 2000-033070 A | 2/2000 | |
| JP | 2003135386 | 5/2003 | |
| JP | 2004226627 | 8/2004 | |
| JP | 2006-523513 A | 10/2006 | |
| WO | WO-9600517 | 1/1996 | |
| WO | WO 9732515 A1 * | 9/1997 | ............... A61B 1/00 |
| WO | WO-9951153 | 10/1999 | |
| WO | WO-0106943 | 2/2001 | |
| WO | WO-0137915 | 5/2001 | |
| WO | WO-03041761 | 5/2003 | |
| WO | WO-2004091689 | 10/2004 | |
| WO | WO-2006126268 | 11/2006 | |
| WO | WO-2006130422 | 12/2006 | |
| WO | WO-2007043118 | 4/2007 | |
| WO | WO-2007043123 | 4/2007 | |
| WO | WO-2007050370 | 5/2007 | |
| WO | WO-2007057962 | 5/2007 | |
| WO | WO-2007057963 | 5/2007 | |

OTHER PUBLICATIONS

"Canadian Application Serial No. 2522170, Office Action mailed Jun. 17, 2010", 2 pgs.

"Canadian Application Serial No. 2522170, Office Action Response filed Jul. 14, 2010 to Office Action dated Jun. 17, 2010", 4 pgs.

"European Application Serial No. 04750115.0, Invitation to Proceed dated Jan. 4, 2010", 1 pg.

"European Application Serial No. 04750115.0, Office Action mailed Apr. 12, 2010", 10 Pgs.

"European Application Serial No. 04750115.0, Reply filed Mar. 3, 2010 to Office Actions of Dec. 18, 2009 and Jan. 4, 2010", 20 pgs.

"European Application Serial No. 06826140.3, Response filed Oct. 13, 2009 to Communication dated Aug. 4, 2009", 8 pgs.

"European Application Serial No. 06826140.3, Communication mailed Jun. 29, 2010", 4 pgs.

"Indian Patent Application Serial No. 2625/CHENP/2005, First Examination Report mailed Jan. 9, 2007", 2 pgs.

"Japanese Application No. 2006-510019, Response filed May 13, 2010 to Office Action mailed Jan. 19, 2010", (w/ English Translation of Amended Claims), 13 pgs.

(56) References Cited

OTHER PUBLICATIONS

"Japanese Application Serial No. 2006-510019, Final Office Action mailed Jun. 8, 2010", (w/ English Translation), 4 pgs.
"Singapore Patent Application No. 200506197-3, Examination Report dated Nov. 20, 2007", 4 pgs.
"Singapore Patent Application No. 200506197-3, Response filed Feb. 15, 2008 to Examination Report dated Nov. 20, 2007", 54 pgs.
"Singapore Patent Application No. 200506197-3, Response filed Jul. 3, 2007 to Invitation to Respond to Written Opinion mailed Feb. 7, 2007", 9 pgs.
"PCT Application No. PCT/US06/40617, International Search Report mailed Oct. 3, 2007", 4 pgs.
"PCT Application No. PCT/US06/40617, Wrriten Opinion mailed Oct. 3, 2007", 12 pgs.
Amendment and Response mailed Jun. 14, 2005 in U.S. Appl. No. 10/823,141, 16 pgs.
First Examination Report mailed Jan. 9, 2007 in Indian Patent Application No. 2625/CHENP/2005, 2 pgs.
Interview Summary mailed Jun. 27, 2005 in U.S. Appl. No. 10/823,141, 2 pgs.
Invitation to Respond to Written Opinion mailed Feb. 7, 2007 in Singapore Patent Application No. 200506197-3, 4 pgs.
Response to Office Action mailed Jul. 3, 2007 in Singapore Patent Application No. 200506197-3, 9 pgs.
"Canadian Application Serial No. 2,522,170, Notice of Allowance mailed Sep. 29, 2010", 1 pg.
"Japanese Application Serial No. 2006-510091, Notice of Allowance mailed Aug. 31, 2010".
"U.S. Appl. No. 11/260,342, Non-Final Office Action mailed Oct. 26, 2009", 11 pgs.
"U.S. Appl. No. 11/260,342, Final Office Action mailed Jan. 12, 2010", 6 pgs.
"U.S. Appl. No. 11/260,342, Response filed Jan. 12, 2010 to Final Office Action mailed Jan. 12, 2010", 21 pgs.
"U.S. Appl. No. 11/260,342, Response filed Nov. 6, 2009 to Non-Final Office Action mailed Oct. 26, 2009", 29 pgs.
"U.S. Appl. No. 11/260,342, Response filed Aug. 27, 2009 to Restriction Requirement mailed Aug. 12, 2009", 24 pgs.
"U.S. Appl. No. 11/260,342, Restriction Requirement mailed Aug. 12, 2009", 11 pgs.
"U.S. Appl. No. 11/260,342, Notice of Allowance mailed Jan. 29, 2010", 6 pgs.
"European Application Serial No. 06826140.3, Supplementary Partial European Search Report mailed Jul. 16, 2009", 7 pgs.
"European Application Serial No. 04750115.0, Supplementary Partial European Search Report mailed Dec. 18, 2009", 4 pgs.
"Israeli Application Serial No. 170833, Office Action mailed Jan. 14, 2009", 4 pgs.
"Israeli Application Serial No. 170833, Response filed May 11, 2009 to Office Action mailed Jan. 14, 2009", 4 pgs.
"Japanese Application No. 2006-510019, Office Action mailed Jan. 19, 2010" (w/ English Translation), 5 pgs.
"Mexican Application No. PA/a/2005/011024, Office Action", (2009), 3 pgs.
"Mexican Application Serial No. PA/a/2005/011024, Response filed Oct. 20, 2008 to Office Action dated Aug. 15, 2008", 10 pgs.
Non-final office action mailed Mar. 15, 2005 in U.S. Appl. No. 10/823,141, 5 pgs.
International Search Report mailed Apr. 15, 2005 in Application No. PCT US04 11466,3 pgs.
Notice of Allowance mailed Jul. 14, 2005 in U.S. Appl. No. 10/823,141, 3 pgs.
Written Opinion mailed Apr. 15, 2005 in Application No. PCT US04 11466, 3 pgs.
Ingram, Mark, et al., "Mechanics of the whole skin locomotion mechanism concentric solid tube model: the effects of geometry and friction on the efficiency and force transmission characteristics", *Proceedings of the IDETC/CIE 2006; ASME 2006 International Design Engineering Technical Conferences & Computers and Information in Engineering Conference* Sep. 10-13, 2006, 1-6.
Ingram, Mark E., "Whole skin locomotion inspired by amoeboid motility mechanisms: mechanics of the cocentric solid tube model", *Masters Thesis, Virginia Polytechnic Institute and State University*, (Aug. 10, 2006), 48 pgs.
Kassim, Irwan, et al., "Review of locomotion techniques for robotic colonoscopy", *Proceedings of the 2003 IEEE Internatinal Conference on Robotics and Automation*, Taipei, Taiwan, Sep. 14-19, 2003, 1086-91.
Phee, S J., "Locomotion and steering aspects in automation of colonoscopy", *IEEE Engineering in Medicine and Biology*, (Nov.-Dec. 1997),85-96.
"International Application Serial No. PCT/US2006/040617, International Preliminary Report on Patentability mailed May 8, 2008", 12 pgs.
"Response filed Jan. 9, 2008 to Second Examination Report mailed Jan. 7, 2008 in Indian Patent Application No. 2625/CHENP/2005", 6 pgs.
"Response filed Nov. 28, 2007 to First Examination Report mailed Jan. 9, 2007 in Indian Patent Application No. 2625/CHENP/2005", 11 pgs.
"Second Examination Report mailed Jan. 7, 2008 in Indian Patent Application No. 2625/CHENP/2005", 2 pgs.
Office Action issued May 8, 2012 by the Israeli Patent Office in counterpart Israeli Application No. 215409.
Japanese Office Action dated Apr. 17, 2012 issued by the Japanese Office Action in Japanese Application No. 2008-537771.

\* cited by examiner

SELF-PROPELLABLE ENDOSCOPIC APPARATUS AND METHOD

RELATED APPLICATIONS

The present application is a continuation of U.S. patent application Ser. No. 11/260,342, filed Oct. 27, 2005, now U.S. Pat. No. 7,736,300 which is a continuation-in-part of U.S. patent application Ser. No. 10/823,141, filed Apr. 13, 2004 now U.S. Pat. No. 6,971,990 which, in turn, claims the benefit of Provisional Patent Application, Ser. No. 60/462,787, filed Apr. 14, 2003, which are incorporated herein by reference in their entirety.

FIELD OF THE INVENTION

This invention relates to an apparatus useful in medical and non-medical applications to introduce accessory devices into collapsible and non-collapsible, body cavities or canals, pipes, lumens and other generally tubular spaces or environments. More particularly, the invention relates to a propulsion system for endoscopic systems.

BACKGROUND OF THE INVENTION

An endoscope is any instrument used to obtain a view of the interior of a patient's body using a variety of means to capture and transmit the view to an observer. Endoscopes can also be used to perform a variety of diagnostic and interventional procedures such as biopsies and other small surgical procedures. Examples of endoscopes include: a colonoscope used within the colon, a gastroscope used inside the stomach, and a bronchoscope used within the trachea and bronchi. Endoscopes are often inserted into body cavities or lumens via natural orifices but can also be inserted into incisions to gain access to areas of the body where no natural entrance exists.

Traditional endoscopes consist of a rigid or flexible rod or shaft with a means of collecting and transmitting an image from inside the patient's body. The rod or shaft is inserted and pushed to the location of interest. The rod or shaft typically surrounds a number of pathways used to house fiber optic cables and route instruments, catheters, devices, gasses, liquids and other substances in and out of the area of interest.

Traditional endoscopes require a minimal rigidity for successful insertion and work well when the body cavity or canal, or other lumens having curves and turns. However, when it is constricted, convoluted and consists of many curves, as is the case with the colon, it can be difficult or impossible to push the endoscope to its desired location. Steerable articulating endoscopes are often used to make navigation of turns easier; however, the increased friction associated with each additional turn limits the number of turns that can be navigated successfully and ultimately limits the distance an endoscope can be introduced into the patient's body. In addition, the increased force required to complete more turns and corners raises the risk of complications such as bowel perforation as well as the discomfort and pain experienced by the patient. It would be useful to have an apparatus for endoscopic medical procedures that can navigate in such environments and can overcome the physical and procedural limitation of traditional endoscopes. It would further be useful if such an apparatus were self-propelled.

Endoscopic devices may also be utilized in non-medical or commercial and industrial applications to obtain views from or introduce instruments or devices into generally tubular spaces or environments such as lumens, sections of pipe or other structures, which may have a number of curves and turns. Such tubular spaces or environments may be partially occluded or have buildup on their interior surfaces and thus present a irregular internal shape or diameter. To navigate through such spaces and environments, it would be useful to have a device or apparatus that can adapt to the internal shape or diameter of the space or environment into which it is introduced and of further use if the apparatus were self-propelled.

SUMMARY OF THE INVENTION

The invention in it various embodiments is a propulsion apparatus that can be used to transport accessory devices within body cavities or canals, sections of pipe, lumens, and other generally tubular spaces and environments and is generally comprised of a toroid and a powered or motorized frame. The motion of the toroid can be powered or unpowered and the direction and speed may be controlled.

In an embodiment of the invention, the apparatus is comprised of a toroid and a frame. The toroid is a fluid-filled, enclosed ring formed of a flexible material. The enclosed ring defines a central cavity, having an interior volume and presenting an exterior surface and an interior surface which move continuously in opposite directions when the apparatus is in motion.

In one embodiment, the frame is formed of a support structure, a housing structure and a series of at least two sets of interlocking rollers or skids located on the support and housing structures. The support structure is located within the interior volume of the enclosed ring. The housing structure is concentrically and coaxially located relative to the support structure and disposed in the central cavity of the enclosed ring. The rollers or skids are located so as to maintain the two structures in a fixed spatial relationship with the flexible material of the enclosed ring being positioned between the two structures and the rollers or skids located thereon.

In another embodiment, the frame is formed of a support structure located within the interior volume of the enclosed ring and a series of at least two sets of interlocking rollers or skids located on the support structure. The rollers or skids are located so as to maintain the flexible material of the enclosed ring between them.

In other embodiments of the invention, the apparatus is a propulsion apparatus for transport of accessory devices. The apparatus is comprised of a toroid and a powered frame. The toroid is a fluid-filled, enclosed ring formed of a flexible material. The enclosed ring defines a central cavity and has an interior volume. The powered frame is formed of a support structure and housing structure or a support structure alone. A series of at least two sets of interlocking rollers or skids located on the support and housing structures or on the support structure in the case there is no housing structure. The support structure is located within the interior volume of the enclosed ring. The housing structure is concentrically and coaxially located relative to the support structure and disposed within the central cavity of the enclosed ring. The rollers or skids are located so as to maintain the two structures in a fixed spatial relationship with the flexible material of the enclosed ring being positioned between the two structures and the rollers or skids located thereon. The rollers may be connected to a power source and when powered provides a motive, directional force to the flexible material.

In its various embodiments, the apparatus of the invention may further comprise at least one accessory device. Depending upon whether the apparatus is to be used for medical or non-medical applications, the at least one accessory device may be selected from the group consisting of endoscopes, cameras, video processing circuitry, fiber optic cables, electronic communication cables, lasers, surgical instruments, medical instruments, diagnostic instruments, instrumentation, sensors, stent catheters, fluid delivery devices, drug delivery devices, electronic devices, tools, sampling devices, assay devices, articulating segments, cables to articulate the articulating segments, other accessory devices, and combinations thereof.

The apparatus of the invention may further comprise a power source connected to the rollers which when powered provide a motive force to the flexible material of the enclosed ring. The power source may be an external power source or an internal power source and may be transmitted through the shaft by various means.

In its various embodiments, the apparatus of the invention may further comprise an accessory tube. The accessory tube has at least one pathway through which accessory devices can be inserted into the patient or connected to external supporting devices.

The apparatus of the invention may be utilized to perform medical or non-medical procedures. In an embodiment of a procedure according to the invention, the apparatus is utilized for medical procedures. The procedure of this embodiment comprising the steps of: introducing a self-propellable, endoscopic apparatus according to the invention into the rectum and anal canal of a patient, the apparatus being equipped with at least one accessory device and connected to at least one external support device; powering the apparatus to propel the apparatus forward through the anal canal and into the colon up to a location in the colon at which at least one medical procedure is to be performed; performing the at least one medical procedure with the at least one accessory device; optionally, serially propelling the apparatus to another location in the colon at which the at least one medical procedure is to be performed and performing said at least one medical procedure; propelling the apparatus backward through the colon and into the anal canal; and removing the apparatus from the patient.

In another embodiment of the invention, an endoscopic procedure is provided. The endoscopic procedure comprises the steps of: introducing a self-propellable, endoscopic apparatus into the generally tubular space or environment, the apparatus being equipped with at least one accessory device and connected to at least one external support device; powering the apparatus to propel and navigate the apparatus forward in the tubular space to a location at which at least one endoscopic procedure is to be performed; performing the at least one endoscopic procedure with the at least one accessory device; optionally, serially propelling the apparatus to another location in the tubular space at which the at least one endoscopic procedure is to be performed and performing said at least one endoscopic procedure; propelling the apparatus backward through tubular space; and removing the apparatus from the tubular space.

DETAILED DESCRIPTION OF THE INVENTION

The self-propellable or self-propelled endoscopic system or apparatus of the invention can be utilized to transport a variety of accessory devices to desired locations within a number of generally tubular spaces and environments, both collapsible and non-collapsible, for medical, industrial and commercial applications. With the system of the invention, an operator, such as a doctor, medical or other technician, can navigate and traverse within generally tubular spaces and/or environments whether of standard or non-standard dimensions and/or of uniform or non-uniform quality that cause difficulty when navigated by pushing a rod or "snake" through it. Examples of such spaces or environments would include, but are not limited to a circular, square, rectangular, or other shaped tube or a tube presenting one or more such shapes along its length that is partially occluded or interior surface of which is irregular, possibly due to material buildup on the surface. And may further include a route with varying diameters, constrictions and curves.

Figure 1:
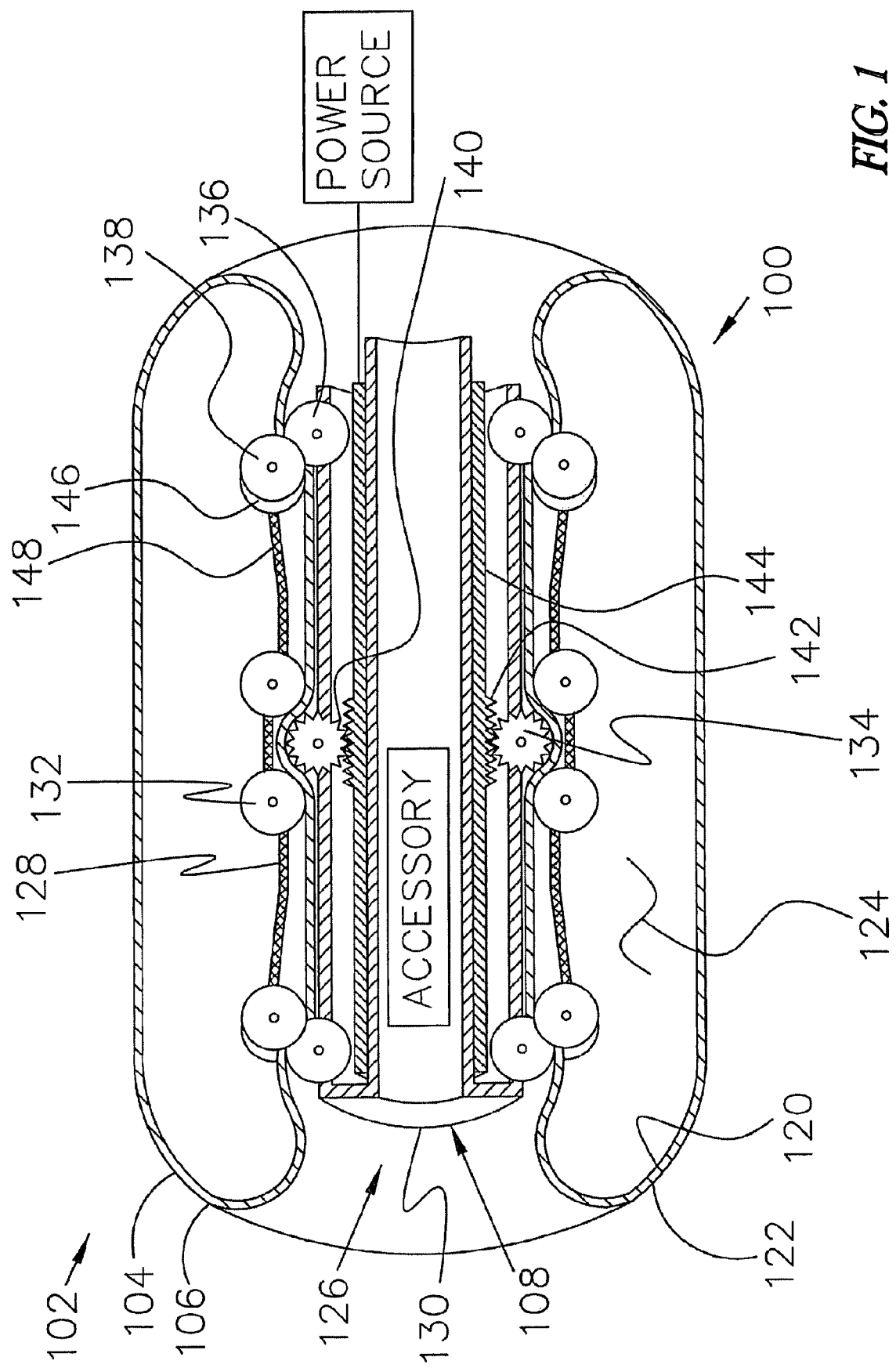
FIG. 1 is a sectional view of an apparatus in accordance with an exemplary embodiment of the apparatus.

FIG. 1 is a sectional view of an apparatus 100 in accordance with an exemplary embodiment of the invention. With reference to FIG. 1 it will be appreciated that the system or apparatus 100 of the invention employs a toroid 102. In the embodiment of FIG. 1, the toroid 102 comprises a bladder 104 of a flexible material 106. The flexible material 106 of bladder 104 has an interior surface 120 and an exterior surface 122. Interior surface 120 of flexible material 106 defines an interior volume 124 of bladder 104. In some embodiments of the present invention, interior volume 124 of bladder 104 contains or is filled with a fluid, a gas, liquid or combination thereof. Exterior surface 122 of flexible material 106 defines a central cavity 126.

The apparatus 100 shown in FIG. 1 also includes a frame 108. Frame 108 both supports and interacts with flexible material 106 of bladder 104. Frame 108 is formed of a support structure 128 and a housing structure 130. With reference to FIG. 1, it will be appreciated that housing structure 130 is disposed in central cavity 126 defined by exterior surface 122 of flexible material 106 of bladder 104. Also with reference to FIG. 1, it will be appreciated that support structure 128 is disposed within interior volume 124 defined by interior surface 120 of flexible material 106 of bladder 104.

Support structure 128 and housing structure 130 each rotatably support a plurality of rollers. In FIG. 1, a pair of motive rollers 134 are shown contacting flexible material 106 of bladder 104. In the embodiment of FIG. 1, rotation of motive rollers 134 will cause flexible material 106 to move relative to the rotational axis of each motive roller 134. In the embodiment of FIG. 1, each motive roller 134 comprises a plurality of teeth 140. With reference to FIG. 1, it will be appreciated that the teeth 140 of each motive roller 134 mate with a first thread 142 of a worm gear 144. Accordingly, in the embodiment of FIG. 1, rotation of worm gear 144 will cause motive rollers 134 to rotate.

The power for rotating motive rollers 134 can be any of a variety of internal or external power sources known to those skilled in the art to be suitable for the given application. In the case of electrical power, the power source may be stored inside the apparatus, or the power may be transmitted via wires from outside the patient or space through an accessory tube (not shown) connected to the apparatus or to one or more electrical motors located inside the housing structure or otherwise operatively connected to motive rollers 134 and/or worm gear 144. The electrical motors, in turn, power the motive rollers 134 and/or worm gear 144. In the case of mechanical power, rollers 134 and/or worm gear 144 may be powered by a thin, flexible, spinning rod or wire powered from a remote motor located outside the patient or space. The motion of the rod or wire is transmitted to the rollers located on the housing structure. Mechanical power may also be transmitted by a spinning spiral or spring component located inside or outside of the apparatus. This power may be manually generated.

In the embodiment of FIG. 1, housing structure 130 rotatably supports a plurality of stabilizing rollers 136. With reference to FIG. 1, it will be appreciated that each stabilizing roller 136 contacts exterior surface 122 of flexible material 106 of bladder 104. In the embodiment of FIG. 1, a suspended stabilizing roller 138 is located proximate each stabilizing roller 136. Each suspended stabilizing roller 138 contacts interior surface 120 of flexible material 106 of bladder 104. In the embodiment of FIG. 1, each suspended stabilizing roller 138 defines a groove 146 that is dimensioned to receive a portion of flexible material 106 and a portion of a stabilizing roller 136.

In the embodiment of FIG. 1, each suspended stabilizing roller 138 is pivotally coupled to an arm 148. In some useful embodiments of the present invention, each arm 148 and suspended stabilizing roller 138 act to bias exterior surface 122 of flexible material 106 against a stabilizing roller 136. Also in FIG. 1, a plurality of suspended motive rollers 132 are disposed proximate each motive roller 134. Each suspended motive roller 132 is pivotally supported by support structure 128. In some useful embodiments of the present invention, support structure 128 and suspended motive rollers 132 act to bias exterior surface 122 of flexible material 106 against motive rollers 134.

For some applications, bladder 104 may be generally longer than it is wide. However, for other applications or depending upon the size or dimension of the space or environment into which the toroid 102 is to be introduced, the bladder 104 may be of substantially equal length and width or may be wider than it is long.

Figure 2:
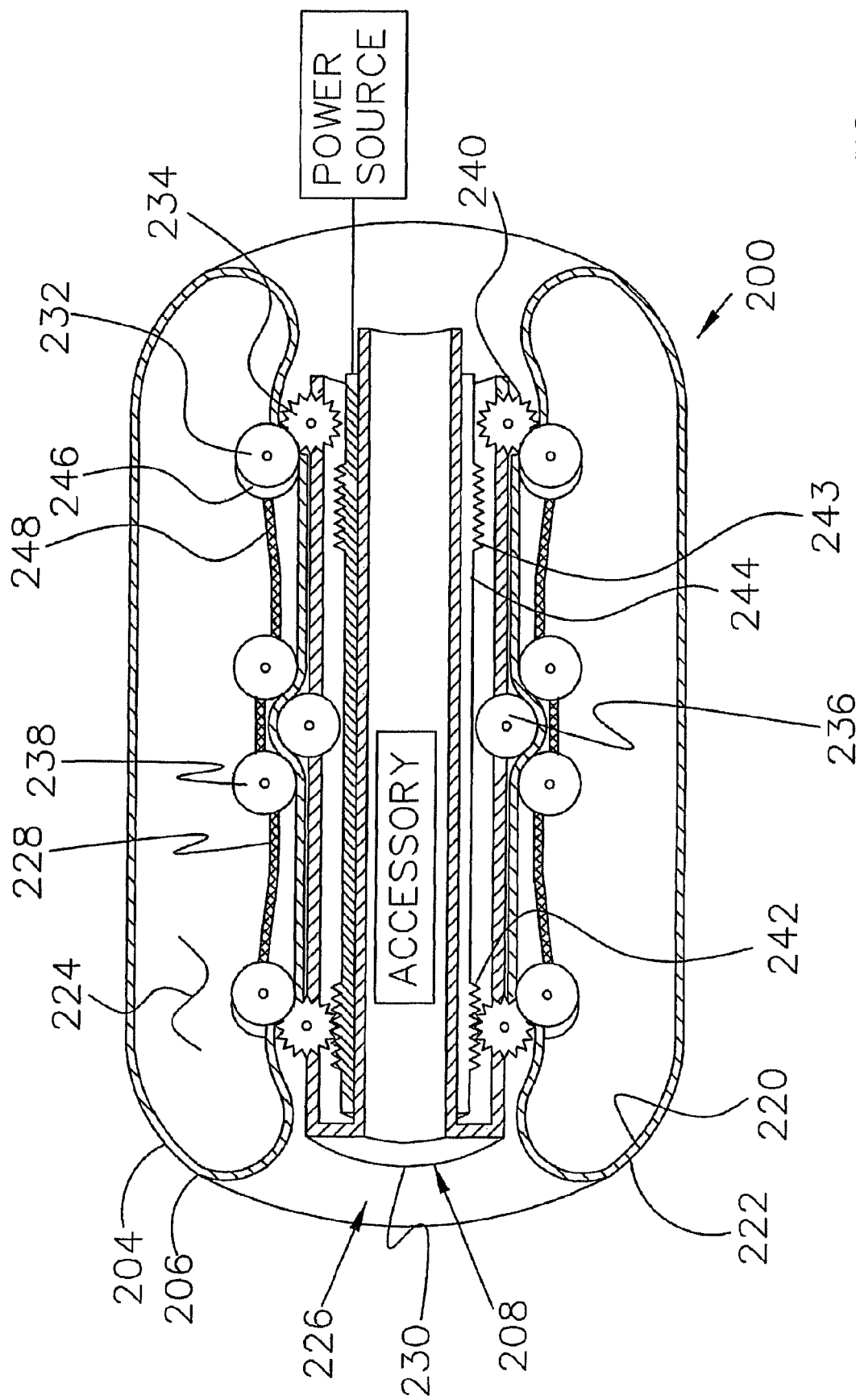
FIG. 2 is a sectional view of an apparatus in accordance with an additional exemplary embodiment of the apparatus.

FIG. 2 is a sectional view of an apparatus 200 in accordance with an additional exemplary embodiment of the invention. With reference to FIG. 2 it will be appreciated that apparatus 200 comprises a bladder 204 that is generally toroidal or ring shaped. Bladder 204 comprises a flexible material 206. Flexible material 206 of bladder 204 has an interior surface 220 and an exterior surface 222. Interior surface 220 of flexible material 206 defines an interior volume 224 of bladder 204. In some embodiments of the present invention, interior volume 224 of bladder 204 contains or is filled with a fluid, a gas, liquid or combination thereof. Exterior surface 222 of flexible material 206 defines a central cavity 226.

The apparatus 200 shown in FIG. 2 also includes a frame 208. Frame 208 both supports and interacts with the flexible material 206 of the bladder 204. Frame 208 comprises a support structure 228 and a housing structure 230. With reference to FIG. 2, it will be appreciated that housing structure 230 is disposed in central cavity 226 defined by exterior surface 222 of flexible material 206 of bladder 204. Also with reference to FIG. 2, it will be appreciated that support structure 228 is disposed within interior volume 224 defined by interior surface 220 of flexible material 206 of bladder 204.

Support structure 228 and housing structure 230 each rotatably support a plurality of rollers. In FIG. 2, a plurality motive rollers 234 are shown contacting flexible material 206 of bladder 204. In the embodiment of FIG. 2, rotation of motive rollers 234 is capable of causing flexible material 206 to move relative to the rotational axis of each motive roller 234. In the embodiment of FIG. 2, each motive roller 234 comprises a plurality of teeth 240. Each motive roller 234 is capable of mating with a worm gear 244.

With reference to FIG. 2, it will be appreciated that worm gear 244 comprises a first thread 242 and a second thread 243. In FIG. 2, the teeth 240 of a first set of motive roller 234 are shown mating with first thread 242 of worm gear 244. Accordingly, in the embodiment of FIG. 2, rotation of worm gear 244 will cause the first set of motive rollers 234 to rotate.

In some embodiments of an apparatus in accordance with an exemplary embodiment of the present invention, a one or more motive rollers are powered by a worm gear. A housing structure of the apparatus may contain a hollow cavity to hold the worm gear in place as illustrated, for example, in FIG. 2. This hollow cavity allows the worm gear 244 to rotate relative to housing structure 230. Worm gear 244 may also move forwards and backward along the central axis of the apparatus in the embodiment of FIG. 2. This movement allows second thread 243 of worm gear 244 to selectively engage a second set of motive rollers while first thread 242 disengages from first set of motive rollers 234. This selective engagement may facilitate forwards and backwards movement of the apparatus. In a variation of this embodiment, the apparatus may be configured so that the first and the second set of motive rollers 234 respectively engage first and second threads 242, 243.

In the embodiment of FIG. 2, housing structure 230 rotatably supports a plurality of stabilizing rollers 236. With reference to FIG. 2, it will be appreciated that each stabilizing roller 236 contacts the exterior surface 222 of flexible material 206 of bladder 204. In the embodiment of FIG. 2, a plurality of suspended stabilizing rollers 238 are located proximate each stabilizing roller 236. Each suspended stabilizing roller 238 contacts interior surface 220 of flexible material 206 of bladder 204. In some useful embodiments of the present invention, each suspended stabilizing roller 238 acts to bias exterior surface 222 of flexible material 206 against a stabilizing roller 236.

With continuing reference to FIG. 2, a suspended motive roller 232 is disposed proximate each motive roller 234. Each suspended motive roller 232 is pivotally supported by support structure 228. In some useful embodiments of the present invention, support structure 228 and suspended motive rollers 232 act to bias exterior surface 222 of flexible material 206 against motive rollers 234.

Various embodiments of housing structure 230 and support structure 228 are possible without deviating from the spirit and scope of the present invention. One exemplary embodiment may be viewed as two tubes positioned with one inside the other. The outer tube being the support structure which is located within the interior volume of the enclosed ring or bladder. The inner tube being the housing structure which is located within the central cavity. In another embodiment exemplary embodiment, either the support structure, the housing structure or both may be comprised of a series of one or more beams that may or may not form the general shape of a cylinder.

The housing and support structures may be, for example, cylindrical with a circular cross section or they may have a cross section in the shape of a square, rectangle, triangle, hexagon or any other shape with straight or curved surfaces or any combination thereof. The frame structures may also be comprised of multiple cross sectional shapes throughout its length. The flexible material 206 of the bladder 204 surface runs between the two tubes which are spaced in fixed relationship relative to each other. The distance between the two tubes is sufficient to accommodate the interlocking rollers or skids and to allow the flexible material 206 for bladder 204 to pass between the support and housing structures even if the material folds over itself or is bunched up.

Figure 3:
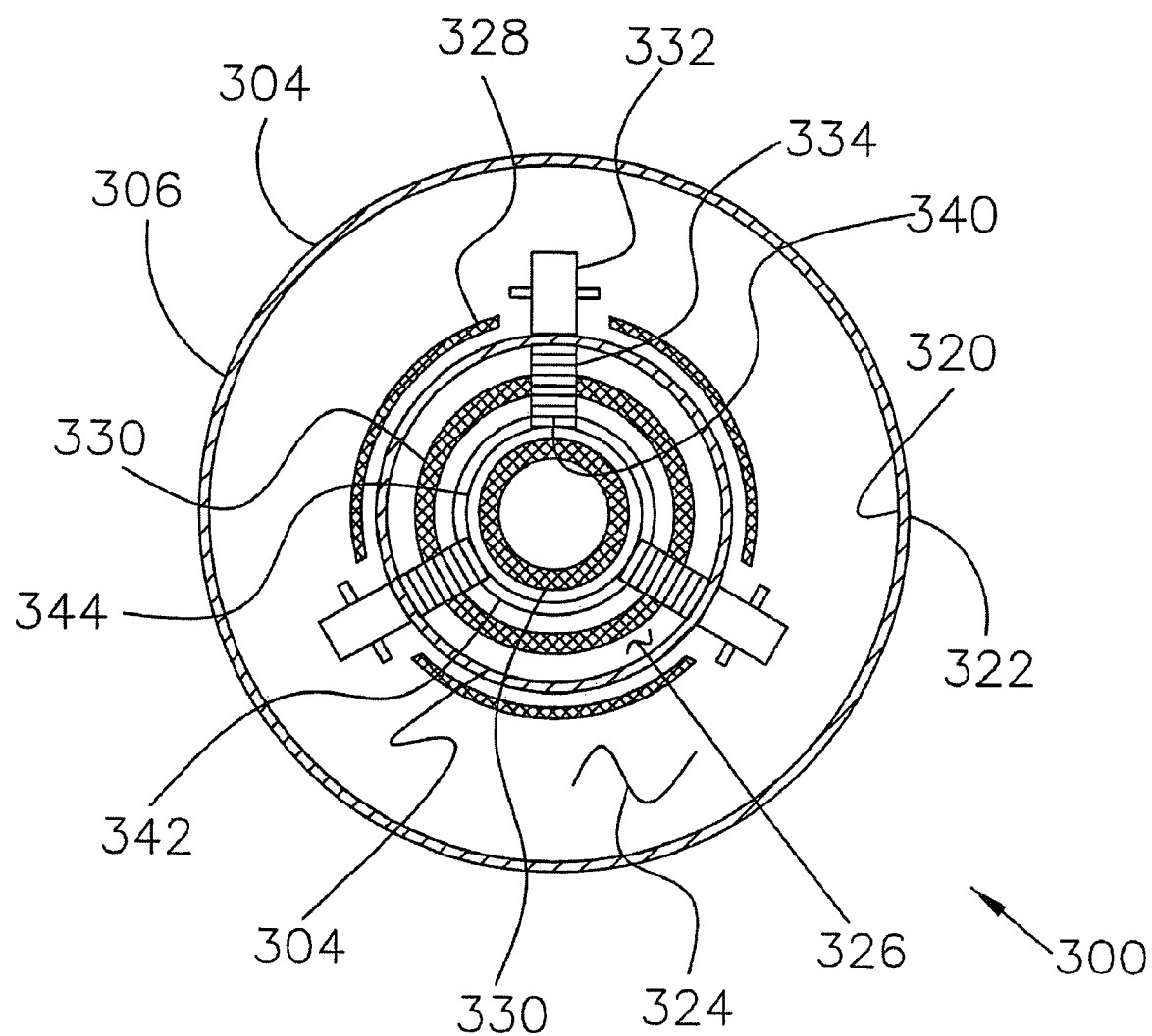
FIG. 3 is an axial cross-sectional view of an apparatus in accordance with an exemplary embodiment of the apparatus.

FIG. 3 is an axial cross-sectional view of an apparatus 300 in accordance with an exemplary embodiment of the present invention. Apparatus 300 includes a bladder 304 comprising a flexible material 306. The flexible material 306 of bladder 304 has an interior surface 320 and an exterior surface 322. Interior surface 320 of flexible material 306 defines an interior volume 324 of bladder 304. In some embodiments of the present invention, interior volume 324 of bladder 304 contains or is filled with a fluid, a gas, liquid or combination thereof. Exterior surface 322 of flexible material 306 defines a central cavity 326.

In the embodiment of FIG. 3, a housing structure 330 is disposed in central cavity 326 defined by exterior surface 322 of flexible material 306 of bladder 304. The housing structure 330 rotatably supports a plurality of motive rollers 334. In FIG. 3, motive rollers 334 are shown contacting exterior surface 322 of flexible material 306. In the embodiment of FIG. 3, each motive roller 334 comprises a plurality of teeth 340. The teeth 340 of each motive roller 334 mate with a thread 342 of a worm gear 344. Thus, in the embodiment of FIG. 3, rotation of worm gear 344 will cause motive rollers 334 to rotate. Also in the embodiment of FIG. 3, rotation of the motive rollers 334 will cause flexible material 306 to move relative to the rotational axis of each motive roller 334.

With continuing reference to FIG. 3, it will be appreciated that a support structure 328 is disposed within an interior volume 324 defined by the interior surface 320 of flexible material 306. In the embodiment of FIG. 3, support structure 328 rotatably supports a plurality of suspended motive rollers 332. In FIG. 3, one suspended motive roller 332 is shown disposed proximate each motive roller 334. Also in FIG. 3, each suspended motive roller 332 can be seen contacting interior surface 320 of flexible material 306 of bladder 304. In some useful embodiments of the present invention, support structure 328 and suspended motive rollers 332 act to bias exterior surface 322 of flexible material 306 against motive rollers 334.

In the exemplary embodiment of FIG. 3, housing structure 330 and support structure 328 each have a generally tubular shape. Thus, housing structure 330 and support structure 328 may be viewed as two tubes positioned with one inside the other. The outer tube being support structure 328 which is located within interior volume 324 defined by interior surface 320 of bladder 304. The inner tube being housing structure 330 which is located within central cavity 326 defined by exterior surface 322 of bladder 304.

It will be appreciated that various embodiments of housing structure 330 and support structure 328 are possible without deviating from the spirit and scope of the present invention. The housing and support structures may be, for example, cylindrical with a circular cross section or they may have a cross section in the shape of a square, rectangle, triangle, hexagon or any other shape with straight or curved surfaces or any combination thereof. The frame structures may also be comprised of multiple cross sectional shapes throughout their length. The flexible material 306 of the bladder 304 surface runs between the two structures which are spaced in fixed relationship relative to each other. The distance between the two structures is sufficient to accommodate the interlocking rollers or skids and to allow the flexible material 306 for bladder 304 to pass between the support and housing structures even if the material folds over itself or is bunched Up.

Figure 4:
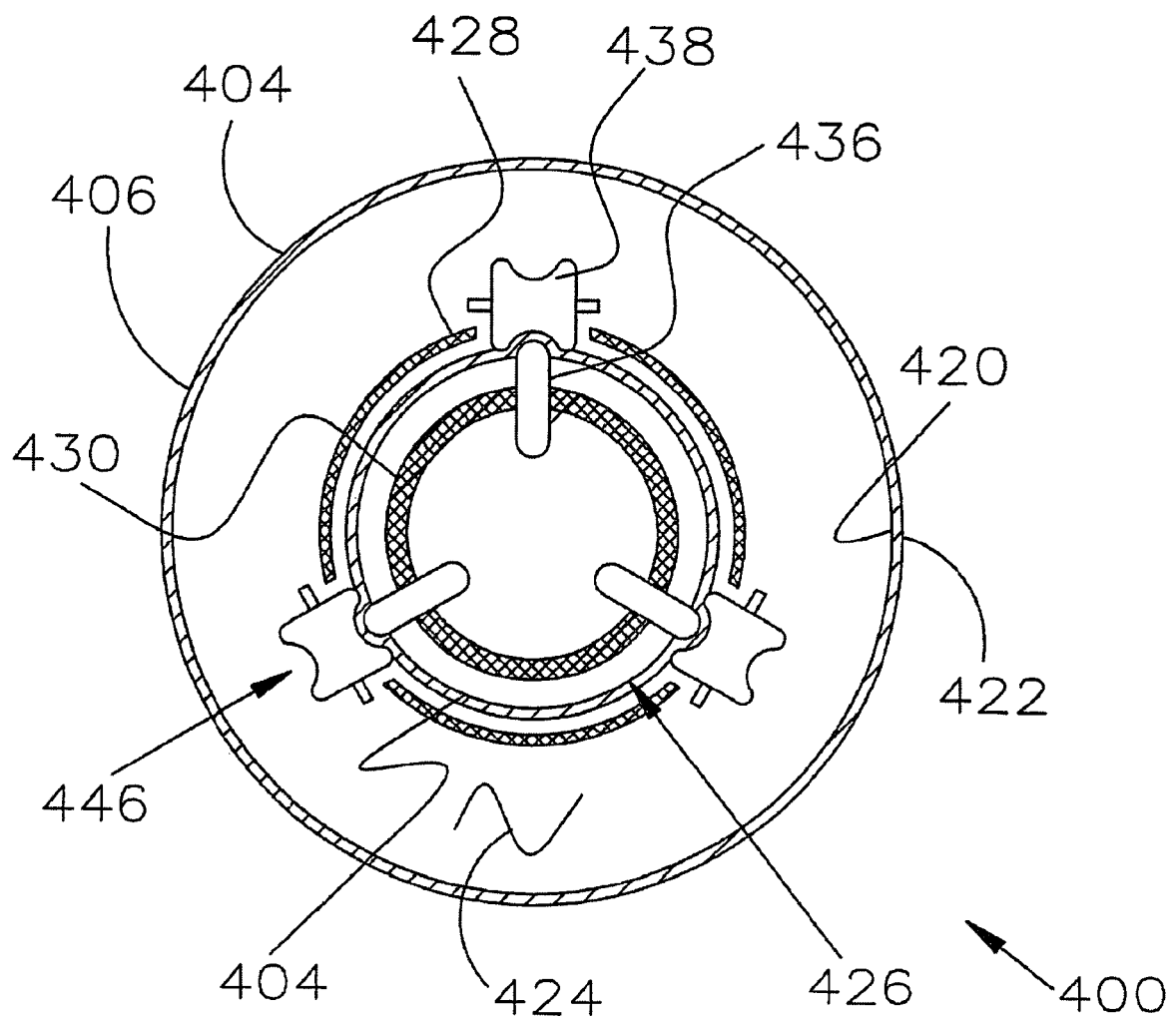
FIG. 4 is an axial cross-sectional view of an apparatus in accordance with an additional exemplary embodiment of the apparatus.

FIG. 4 is an axial cross-sectional view of an apparatus 400 in accordance with an additional exemplary embodiment of the present invention. Apparatus 400 comprises a bladder 404 of a flexible material 406. In FIG. 4 a support structure 428 is shown disposed within an interior volume 424 defined by the interior surface 420 of flexible material 406. In the embodiment of FIG. 4, support structure 428 rotatably supports a plurality of suspended stabilizing rollers 438. With reference to FIG. 4, it will be appreciated that each suspended stabilizing roller 438 contacts the interior surface 420 of flexible material 406 of bladder 404. In some useful embodiments of the present invention, support structure 428 and suspended stabilizing roller 438 act to bias exterior surface 422 of flexible material 406 against a stabilizing roller 436.

In the embodiment of FIG. 4, a housing structure 430 is disposed in a central cavity 426 defined by an exterior surface 422 of flexible material 406 of bladder 404. Housing structure 430 rotatably supports a plurality of stabilizing rollers 436. With reference to FIG. 4, it will be appreciated that each stabilizing roller 436 contacts the interior surface 420 of flexible material 406 of bladder 404. In the embodiment of FIG. 4, each suspended stabilizing roller 438 defines a groove 446 that is dimensioned to receive a portion of flexible material 406 and a portion of a stabilizing roller 436.

Figure 5:
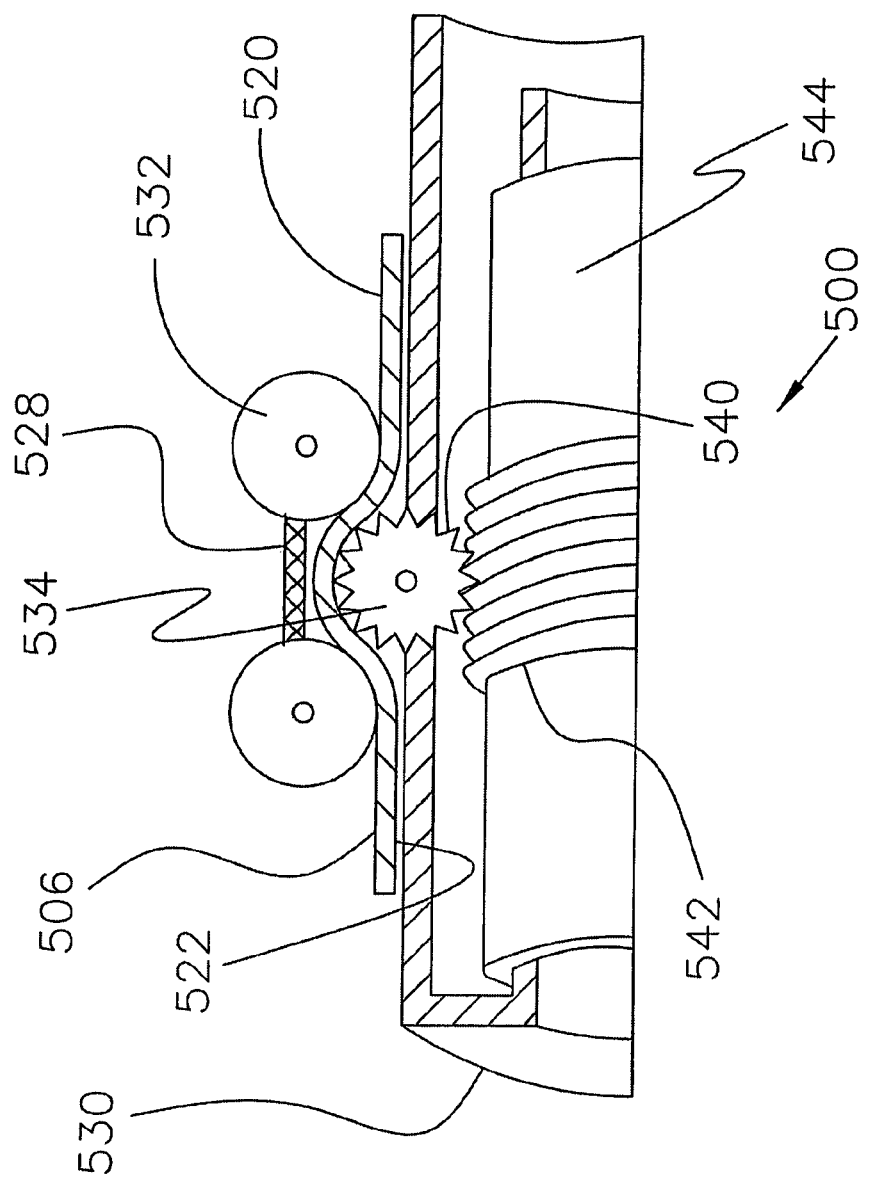
FIG. 5 is an enlarged, partial, cross-sectional view of an apparatus in accordance with an exemplary embodiment of the apparatus.

FIG. 5 is an enlarged, partial, cross-sectional view of an apparatus in accordance with an exemplary embodiment of the invention. Apparatus 500 comprises a housing structure 530 and a support structure 528. Housing structure 530 rotatably supports a motive roller 534 and support structure 528 rotatably supports a plurality of suspended motive rollers 532. A flexible material 506 is disposed between motive roller 534 and suspended motive rollers 532. Flexible material 506 may form, for example, a portion of a bladder in accordance with the present invention. Suspended motive rollers 532 are rotatably supported by a support structure 528. In the embodiment of FIG. 5, housing structure 530 rotatably supports a worm gear 544. A first thread 542 of worm gear 544 engages teeth 540 of motive roller 534. In the embodiment of FIG. 5, rotation of worm gear 544 will cause motive roller 534 to rotate. Rotation of motive roller 534, in turn, causes flexible material 506 to move relative to housing structure 530. With reference to FIG. 5, it will be appreciated that flexible material 506 has an interior surface 520 and an exterior surface 522.

Figure 6:
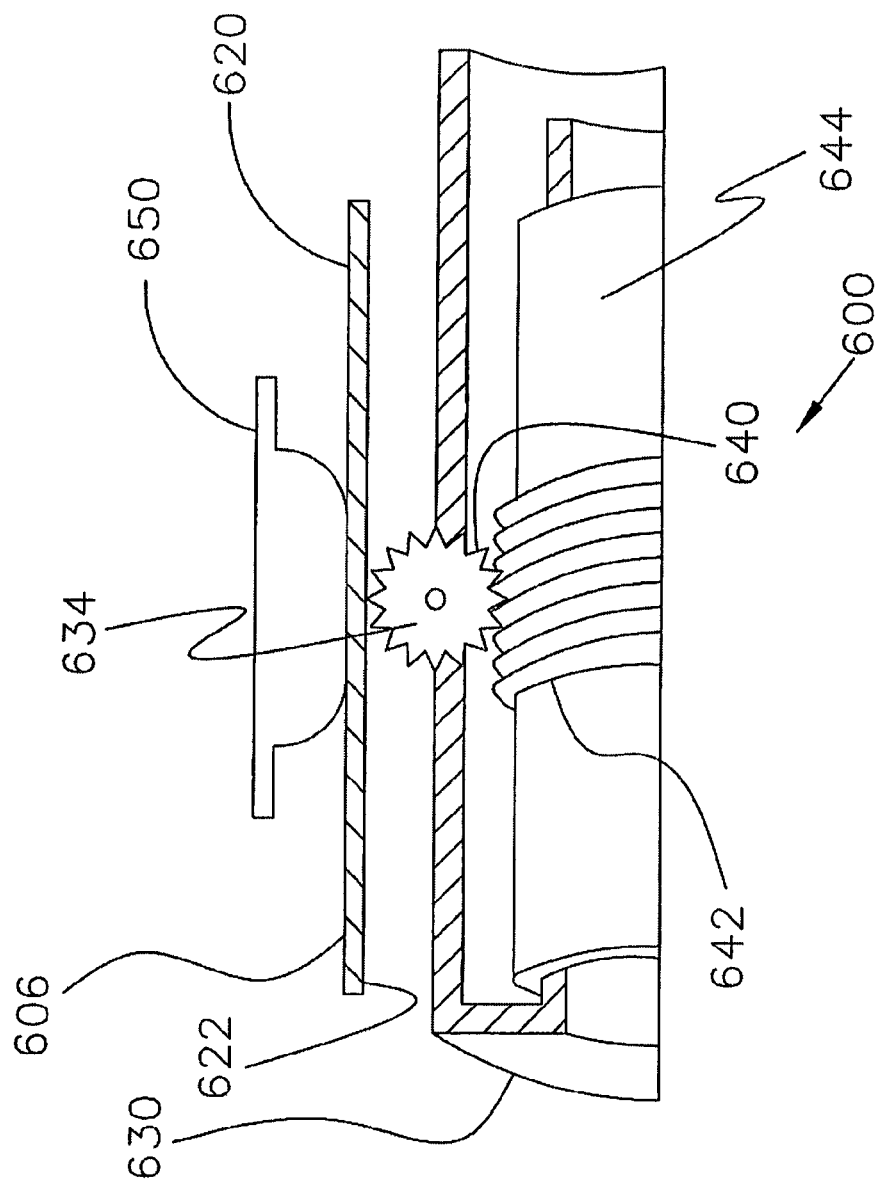
FIG. 6 is an enlarged, partial, cross-sectional view of an apparatus in accordance with an exemplary embodiment of the apparatus.

FIG. 6 is an enlarged, partial, cross-sectional view of an apparatus 600 in accordance with an exemplary embodiment of the invention. Apparatus 600 comprises a housing structure 630 that rotatably supports a worm gear 644. A first thread 642 of worm gear 644 engages the teeth 640 of a motive roller 634. Motive roller 634 is rotatably supported by housing structure 630. A flexible material 606 is disposed between motive roller 634 and a skid 650. Flexible material 606 may form, for example, a portion of a bladder in accordance with the present invention.

In the embodiment of FIG. 6, rotation of worm gear 644 causes rotation of motive roller 634. Rotation of motive roller 634, in turn, causes flexible material 606 to move relative to housing structure 630. With reference to FIG. 6, it will be appreciated that skid 650 contacts an interior surface 620 of flexible material 606. In some useful embodiments of the present invention, skid 650 acts to bias an exterior surface 622 of flexible material 606 against motive roller 634.

Figure 7:
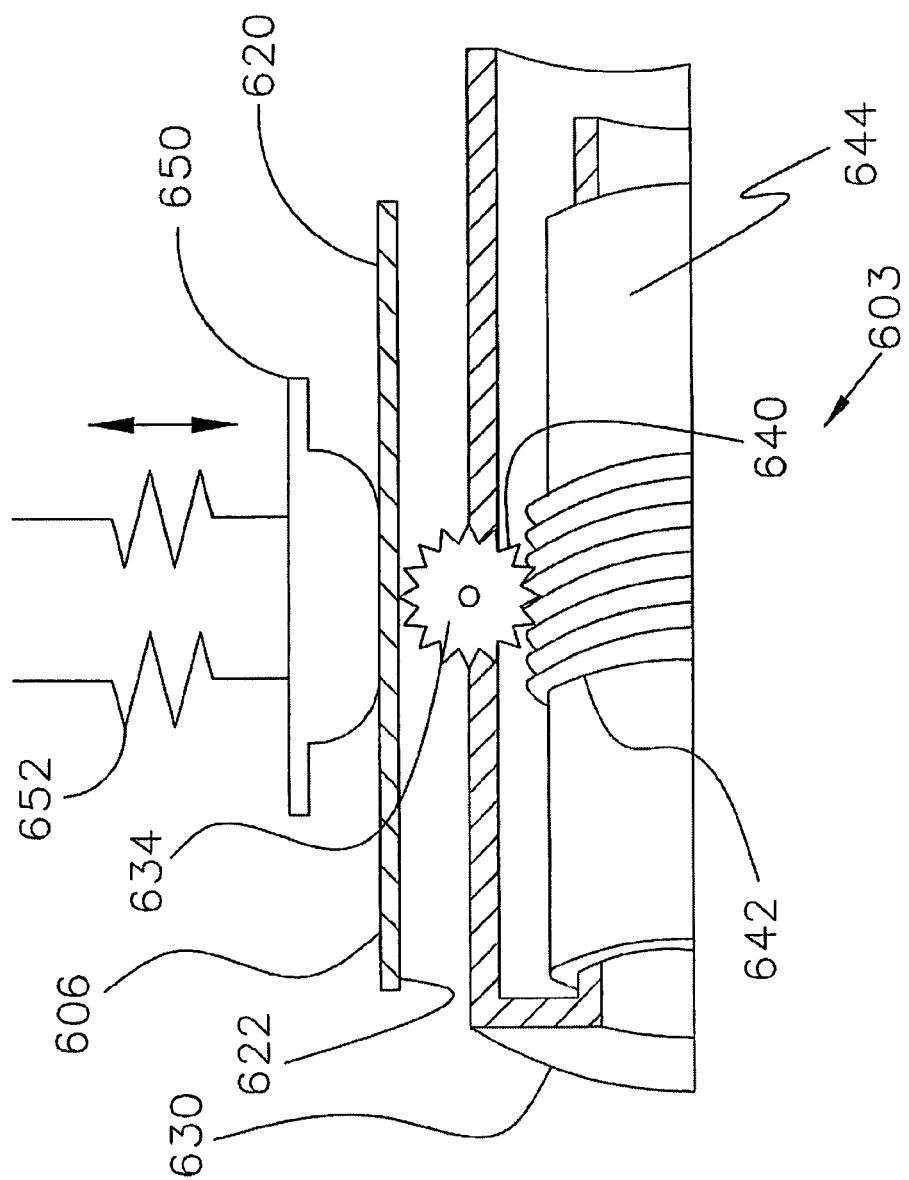
FIG. 7 is an enlarged, partial, cross-sectional view of an apparatus in accordance with an additional exemplary embodiment of the apparatus.

FIG. 7 is an enlarged, partial, cross-sectional view of an apparatus 603 in accordance with an additional exemplary embodiment of the invention. Apparatus 603 comprises a housing structure 630 that rotatably supports a motive roller 634. A flexible material 606 is disposed between motive roller 634 and a skid 650. In the embodiment of FIG. 7, a pair of springs 652 act to bias skid 650 against an interior surface 620 of flexible material 606. Springs 652 are diagrammatically illustrated in FIG. 7. Springs 652 may comprise, for example, sheet metal arms. A compression motion and an extension motion of springs 652 and skid 650 are illustrated with arrows in FIG. 7.

In some useful embodiments of the present invention, skid 650 and springs 652 act to bias an exterior surface 622 of flexible material 606 against motive roller 634. Teeth 640 of motive roller 634 engage a first thread 642 of a worm gear 644 that is rotatably supported by housing structure 630. In the embodiment of FIG. 7, rotation of worm gear 644 causes rotation of motive roller 634. Rotation of motive roller 634, in turn, causes flexible material 606 to move relative to housing structure 630.

Figure 8:
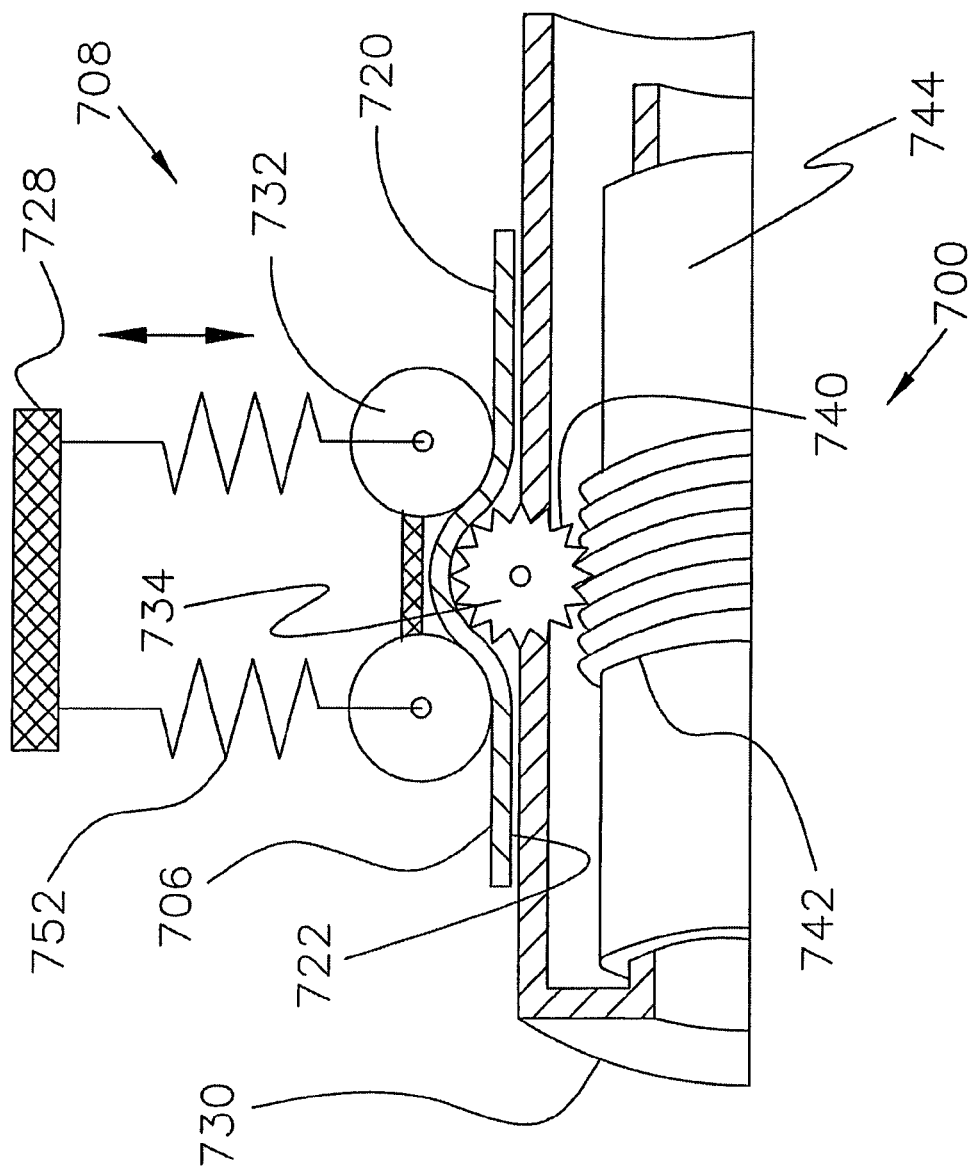
FIG. 8 is an enlarged, partial, cross-sectional view of an apparatus in accordance with an exemplary embodiment of the apparatus.

FIG. 8 is an enlarged, partial, cross-sectional view of an apparatus in accordance with an exemplary embodiment of the invention. Apparatus 700 includes a frame 708 comprising a housing structure 730 and a support structure 728. Housing structure 730 rotatably supports a motive roller 734 and support structure 728 rotatably supports a plurality of suspended motive rollers 732. A flexible material 706 is disposed between motive roller 734 and suspended motive rollers 732.

Suspended motive rollers 732 are rotatably supported by a support structure 728. A pair of springs 752 of support structure 728 are diagrammatically illustrated in FIG. 8. In the embodiment of FIG. 8, springs 752 act to bias suspended motive rollers 732 against an interior surface 720 of flexible material 706. Springs 752 may comprise, for example, sheet metal arms. A compression motion and an extension motion of springs 752 and suspended motive rollers 732 are illustrated with arrows in FIG. 8.

In the embodiment of FIG. 8, housing structure 730 rotatably supports a worm gear 744. A first thread 742 of worm gear 744 engages teeth 740 of motive roller 734. In the embodiment of FIG. 8, rotation of worm gear 744 will cause motive roller 734 to rotate. Rotation of motive roller 734, in turn, causes flexible material 706 to move relative to housing structure 730.

Figure 9:
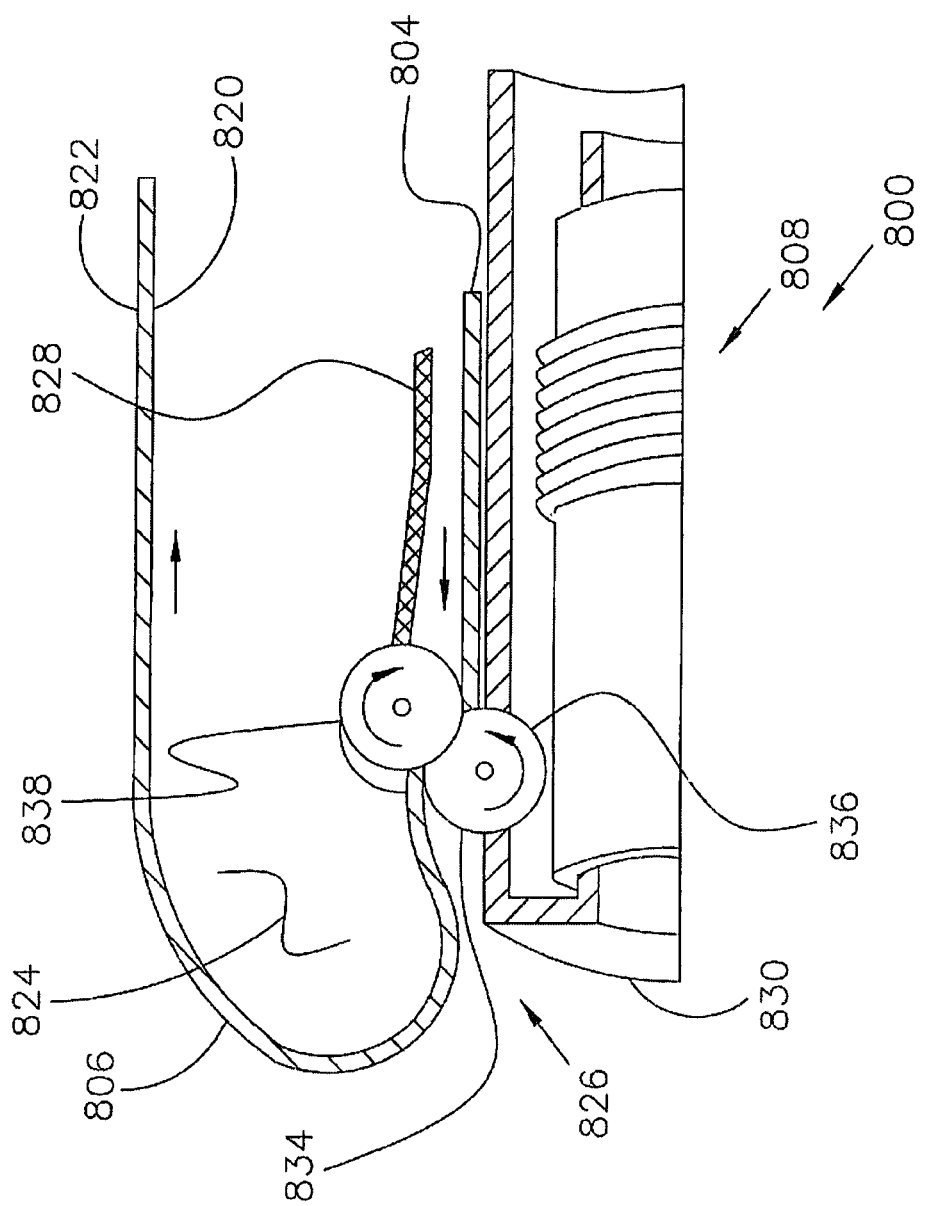
FIG. 9 is an enlarged, partial cross-sectional view of an apparatus in accordance with an additional exemplary embodiment of the apparatus.

FIG. 9 is an enlarged, partial cross-sectional view of an apparatus 800 in accordance with an additional exemplary embodiment of the invention. With reference to FIG. 9 it will be appreciated that apparatus 800 comprises a bladder 804. In some embodiments of the present invention, bladder has a generally toroidal or ring shape. Bladder 804 comprises a flexible material 806. Flexible material 806 of bladder 804 has an interior surface 820 and an exterior surface 822. Interior surface 820 of flexible material 806 defines an interior volume 824 of bladder 804. In some embodiments of the present invention, interior volume 824 of bladder 804 contains or is filled with a fluid, a gas, liquid or combination thereof. Exterior surface 822 of flexible material 806 defines a central cavity 826.

The apparatus 800 shown in FIG. 9 also includes a frame 808. Frame 808 both supports and interacts with the flexible material 806 of the bladder 804. Frame 808 comprises a support structure 828 and a housing structure 830. In the embodiment of FIG. 9, housing structure 830 rotatably supports a stabilizing roller 836 and support structure rotatably supports a suspended stabilizing roller 838. With reference to FIG. 9, it will be appreciated that suspended stabilizing roller 838 contacts the interior surface 820 of flexible material 806 of bladder 804. Stabilizing roller 836 is shown contacting an exterior surface 822 of flexible material 806 of bladder 804. The rotation of the rollers and the movement of flexible material 806 are illustrated with arrows in FIG. 9.

Figure 10:
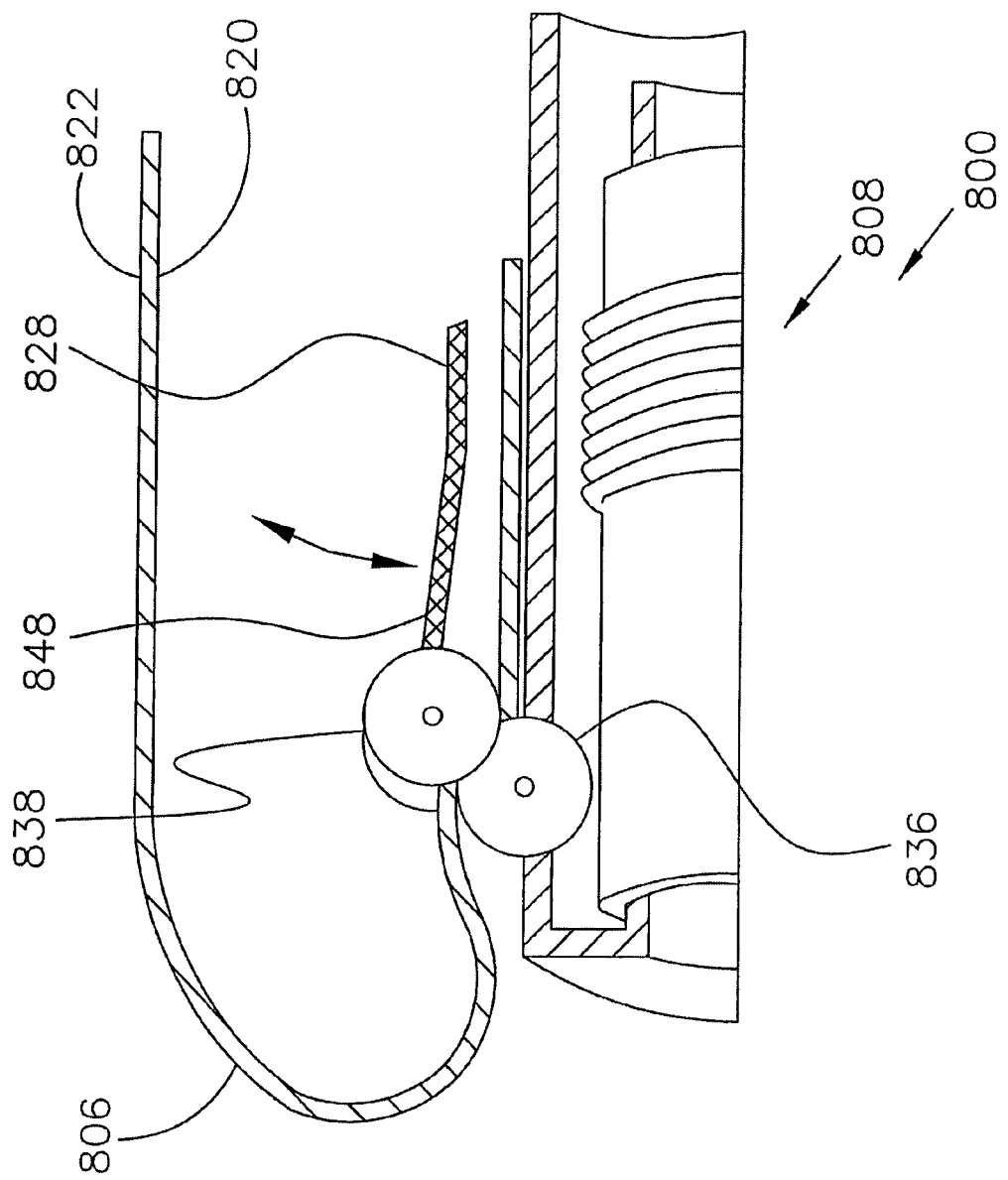
FIG. 10 is an additional enlarged, partial cross-sectional view of the apparatus shown in the previous figure.

FIG. 10 is an additional enlarged, partial, cross-sectional view of apparatus 800 shown in the previous figure. In some useful embodiments of the present invention, suspended stabilizing roller 838 acts to bias exterior surface 822 of flexible material 806 against stabilizing roller 836. In the embodiment of FIG. 10, an arm 848 of Support structure 828 acts to bias suspended stabilizing roller 838 against interior surface 820 of flexible material 806. A flexing motion of arm 848 is illustrated using arrows in FIG. 10.

Figure 11:
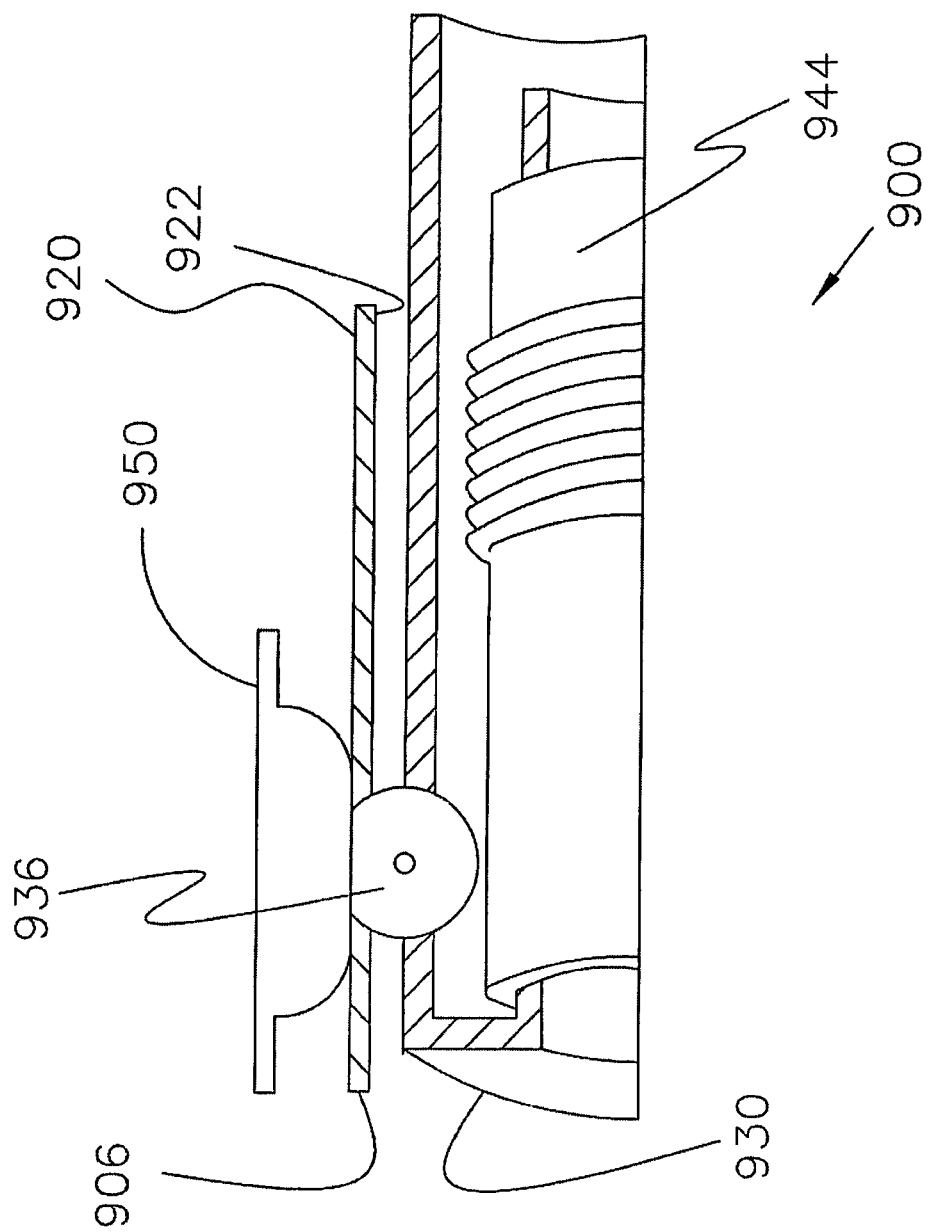
FIG. 11 is an enlarged, partial, cross-sectional view of an apparatus in accordance with an exemplary embodiment of the apparatus.

FIG. 11 is an enlarged, partial, cross-sectional view of an apparatus 900 in accordance with an exemplary embodiment of the invention. Apparatus 900 comprises a housing structure 930 that rotatably supports a worm gear 944. A stabilizing roller 936 is rotatably supported by housing structure 930. A flexible material 906 is disposed between stabilizing roller 936 and a skid 950. Flexible material 906 may form, for example, a portion of a bladder in accordance with the present invention. With reference to FIG. 11, it will be appreciated that skid 950 contacts an interior surface 920 of flexible material 906. In some useful embodiments of the present invention, skid 950 acts to bias an exterior surface 922 of flexible material 906 against stabilizing roller 936.

Figure 12:
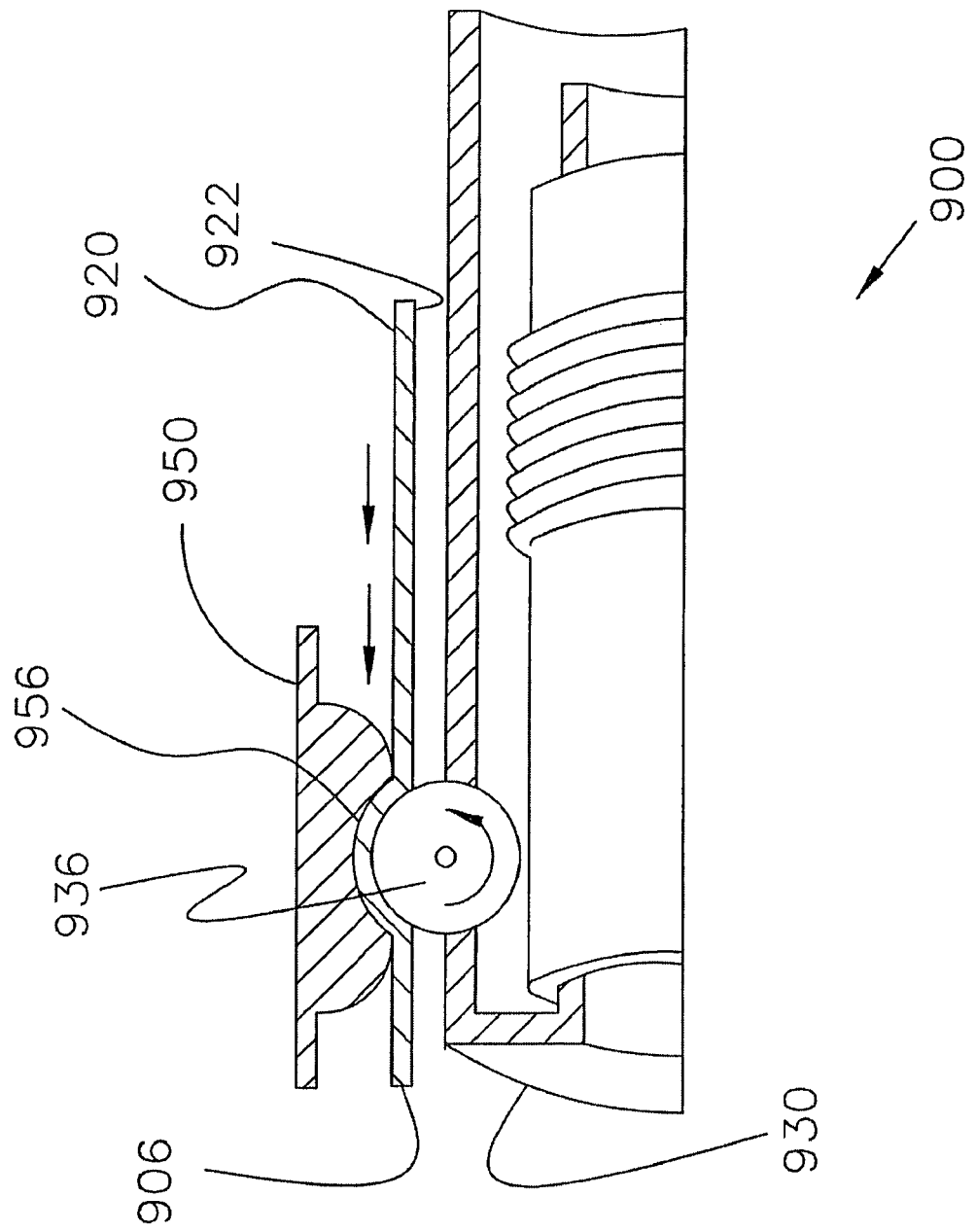
FIG. 12 is an additional enlarged, partial cross-sectional view of the apparatus shown in the previous figure.

FIG. 12 is an additional enlarged, partial cross-sectional view of apparatus 900 shown in the previous figure. Skid 950 of apparatus 900 is shown in cross section in FIG. 12. With reference to FIG. 12, it will be appreciated that skid 950 defines a depression 956. In the embodiment of FIG. 12, depression 956 is dimensioned to receive a portion of flexible material 906 and a portion of stabilizing roller 936. The rotation of stabilizing roller 936 and the motion of flexible material 906 are illustrated with arrows in FIG. 12.

Figure 13:
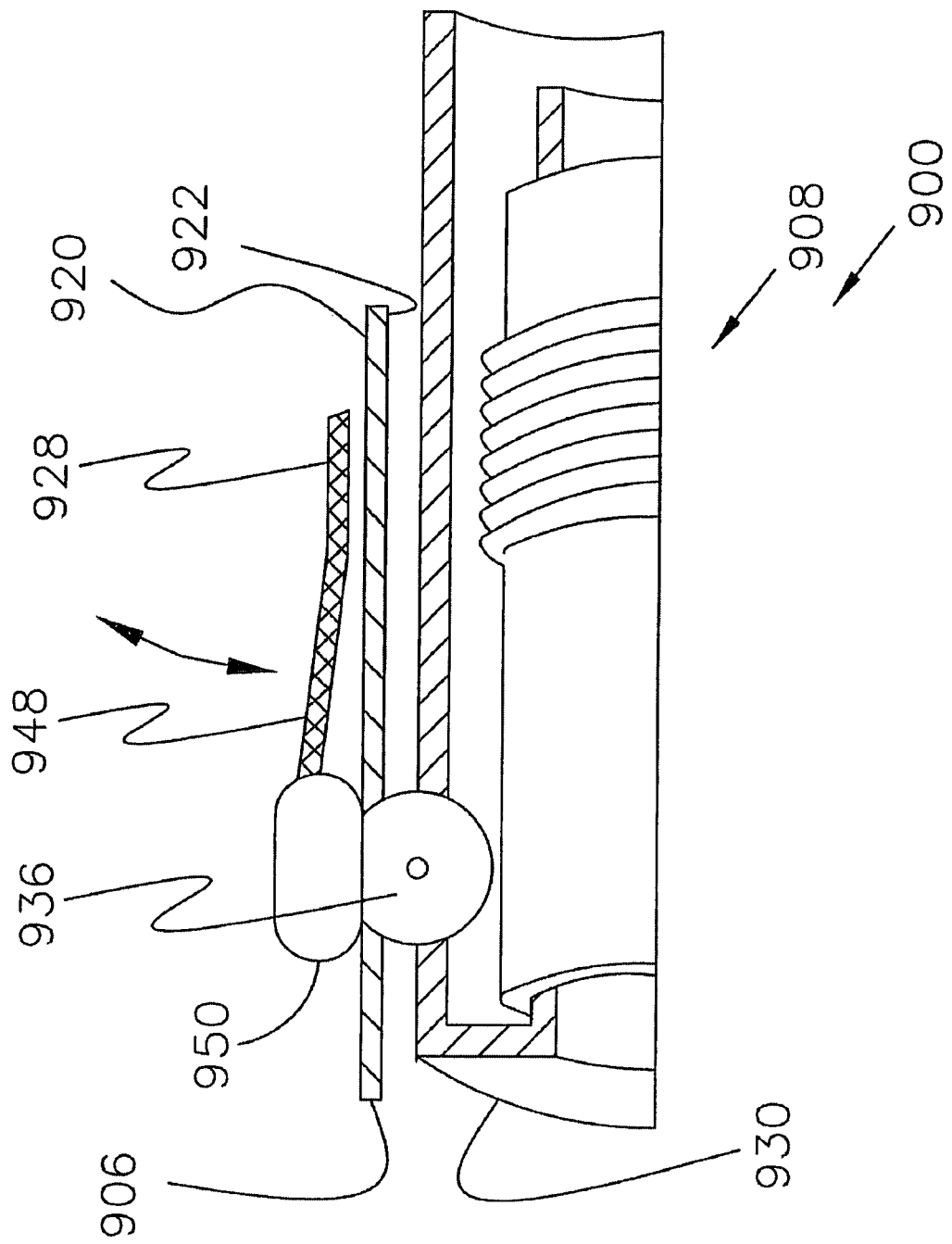
FIG. 13 is an enlarged, partial, cross-sectional view of an apparatus in accordance with an additional exemplary embodiment of the apparatus.

FIG. 13 is an enlarged, partial cross-sectional view of apparatus 900 in accordance with an additional exemplary embodiment of the present invention. Apparatus 900 includes a frame 908 comprising a housing structure 930 and a support structure 928. A stabilizing roller 936 is rotatably supported by housing structure 930. A flexible material 906 is disposed between stabilizing roller 936 and a skid 950. With reference to FIG. 13, it will be appreciated that skid 950 contacts an interior surface 920 of flexible material 906. In some useful embodiments of the present invention, skid 950 acts to bias exterior surface 922 of flexible material 906 against stabilizing roller 936. In the embodiment of FIG. 13, an arm 948 of support structure 928 acts to bias skid 950 against interior surface of flexible material 906. A flexing motion of arm 948 is illustrated using an arrow in FIG. 13.

Figure 14:
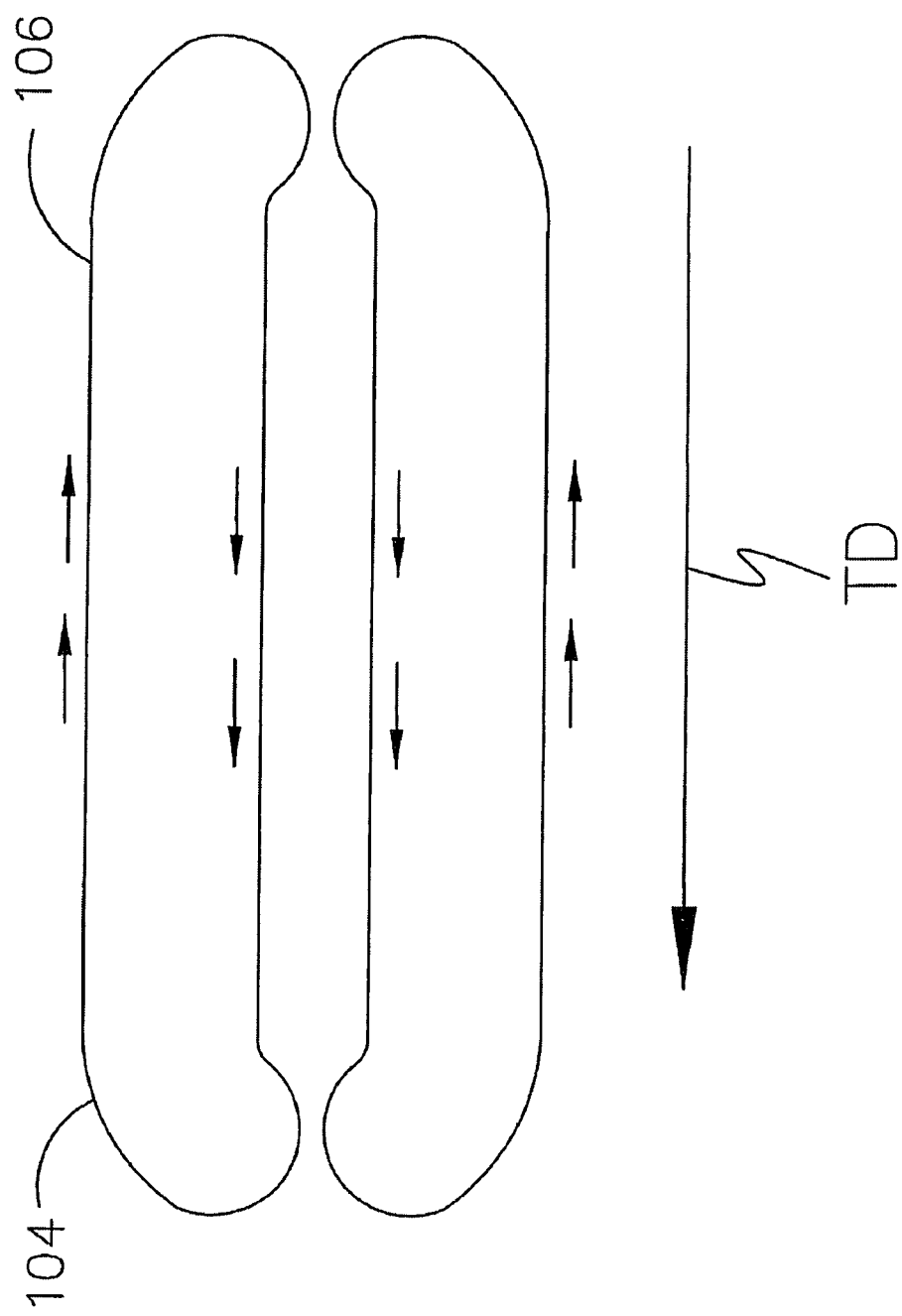
FIG. 14 is a cross-sectional view of a bladder in accordance with an exemplary embodiment of the apparatus.

FIG. 14 is a cross-sectional view of a bladder 104 in accordance with an exemplary embodiment of the present invention. Bladder 104 comprises a flexible material 106. The movement of flexible material 106 is illustrated with arrows in FIG. 14. With reference to FIG. 14, an exterior portion of bladder 104 can be viewed as moving in one direction while an interior portion of bladder 104 is moving in the opposite direction. The result is that the entire shape can move along its central axis while the external material rolls around itself. Thus, the flexible material may be described as circulating around and through the frame in a continuous motion from inside the central cavity long is central axis to the outside where the exterior surface of the flexible material travels along in contact with the interior surface of a generally tubular space or environment or other lumen. A travel direction of bladder 104 is labeled TD in FIG. 14. This motion is well adapted to travel within a generally cylindrical or tubular space, even a collapsible one, such as exists with the colon or rectal canal. The entire object moves with minimal to no slipping because its exterior surface remains in relatively constant or continuous contact with the interior of the space while the interior surface of the flexible materials moves forward in the direction of travel as shown.

Figure 15:
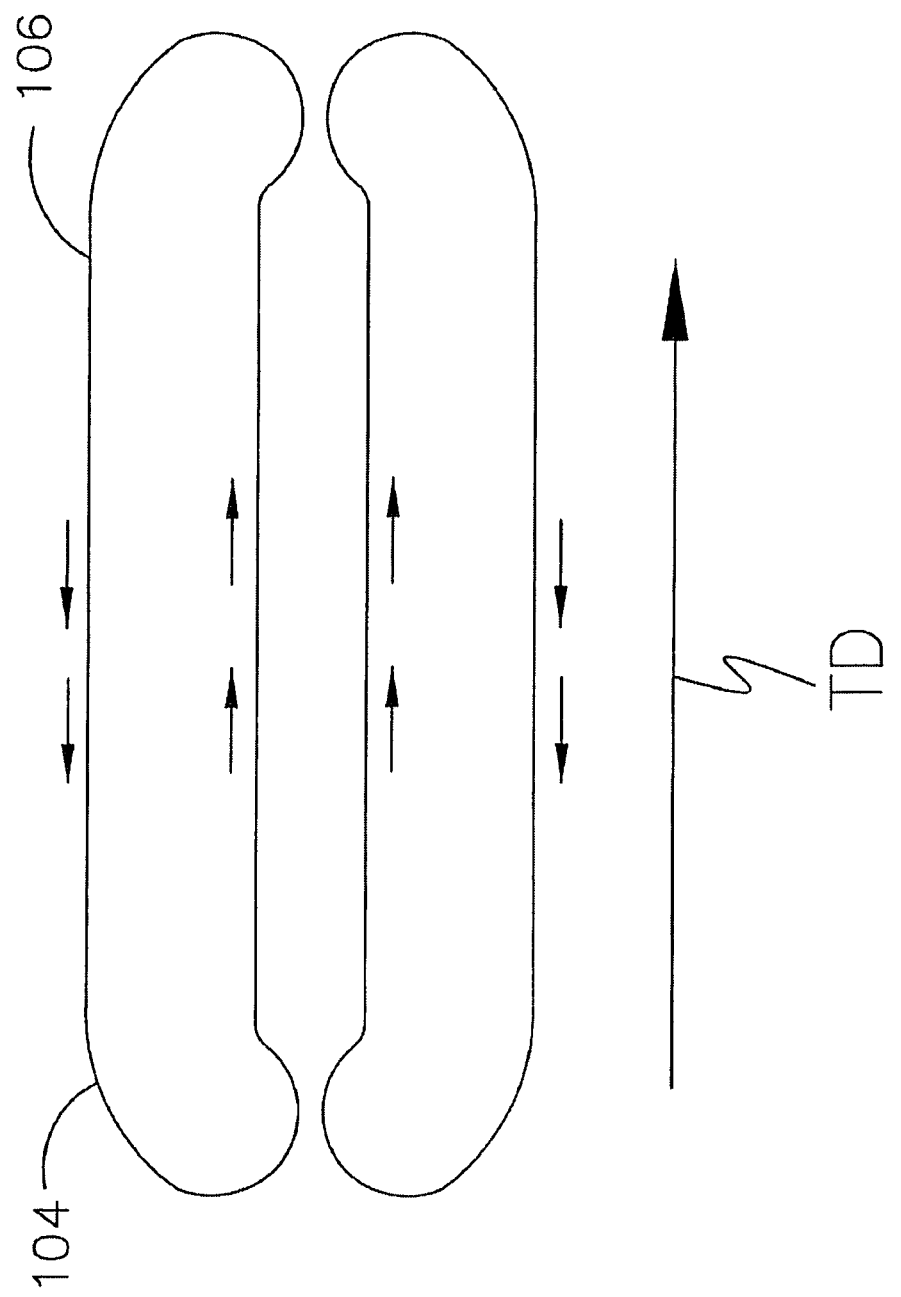
FIG. 15 is an additional cross-sectional view of bladder shown in the previous figure.

FIG. 15 is an additional cross-sectional view of bladder 104 shown in the previous figure. In the embodiment of FIG. 15, bladder 104 is traveling in a second travel direction TD that is generally opposite the travel direction shown in the previous figure. The movement of flexible material 106 of bladder 104 is illustrated with arrows in FIG. 15. With reference to FIG. 15, an exterior portion of bladder 104 can be viewed as moving in one direction while an interior portion of bladder 104 is moving in the opposite direction.

Figure 16A:
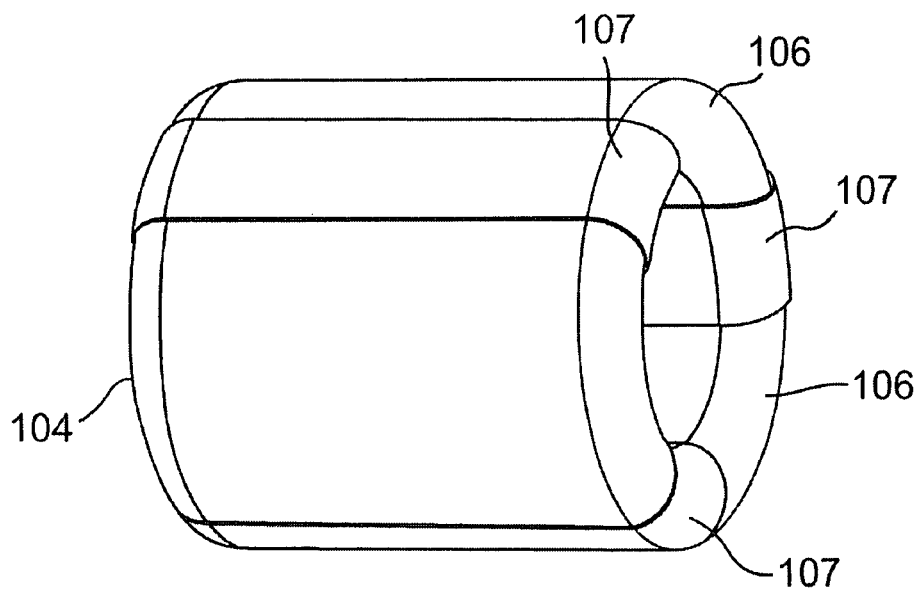
FIGS. 16A and 16B provide an alternate embodiment of the bladder.
Figure 16B:
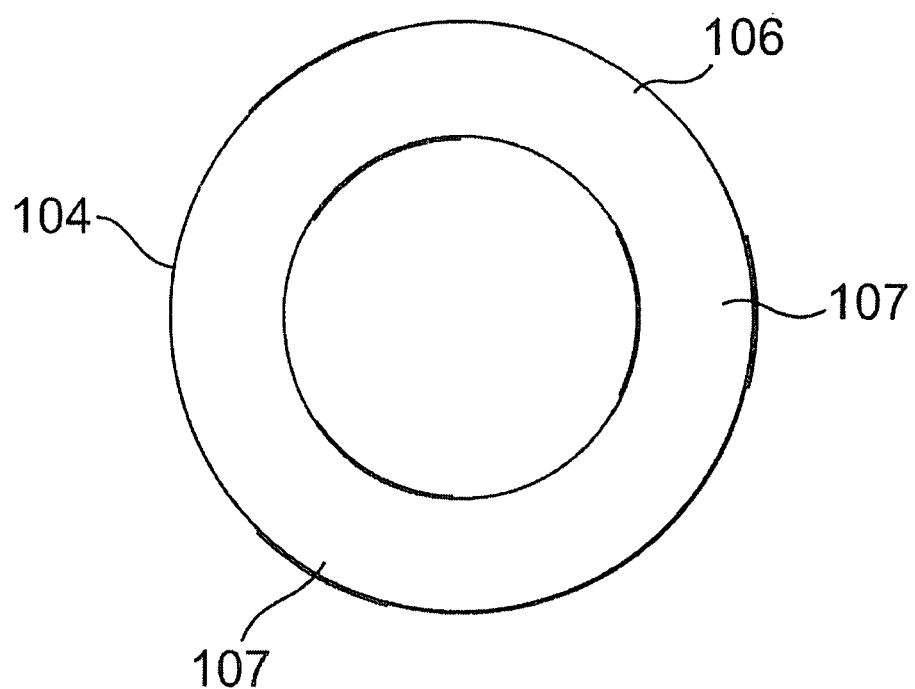

FIGS. 16A and 16B provide illustration of one embodiment of the bladder 104. As described above, the bladder 104 forming the fluid-filled toroid 102 may be comprised of a flexible material 106 in at least one first section of the bladder. In addition, at least one second section 107 of the bladder 104 may be comprised of at least one material that differs from the flexible material section(s) 106 in material composition and/or physical properties. For example, the at least one second section 107 may comprise properties that differ from the flexible material section(s) 106 in, inter alia, thickness, stiffness, texture, surface finish, surface pattern, durometer, flexibility, durability, friction characteristics, color, hydrophilic/hydrophobic tendencies, elasticity, wear characteristics, permeability, melting point, biocompatibility, chemical compatibility and/or chemical solubility. In addition, the at least one second section 107 may be more resistant than the at least one first section 106.

The sections 106 and 107 may be arranged and separated into alternating strips as shown in FIGS. 16A and 16B. Such alternating strips may encircle the toroid as shown comprising the at least one flexible material first section 106 and the at least one second section 107. In the embodiment shown, the at least one second section 107 is arranged in such a manner that the sections 107 travel between a motive roller 134 and suspended motive roller 132 as described above. This arrangement may provide the additional section(s) 107 with a thicker, stiffer and a more wear resistant material or surface finish than that of the first flexible material section(s) 106. In addition, the surface finish of the second section(s) 107 may match the configuration of the plurality of teeth 140 disposed on the motive rollers 134.

The alternating strips of the first flexible material section(s) 106 and second section(s) 107, as illustrated, may thus travel in a continuous looping manner as the toroid's surface circulates around itself in a continuous motion from inside its central cavity along the central axis to the outside where the surface travels in the opposite direction until it again rotates into the central cavity as described above in connection with FIG. 14.

Thus, FIGS. 16A and 16B provide for a bladder 104 consisting of at least one flexible material section 106 and at least one second, more resistant, section 107 that facilitates the movement of the toroid. For example, the at least one second section 107 may be arranged in a striplike fashion so that each such section 107 travels between a motive roller 134 and the associated suspended motive roller 132. In this embodiment, the second section(s) 107 may be thicker, stiffer and/or more wear resistant than the at least one first flexible material section 106. In this embodiment, a higher compression force may be applied downwardly as illustrated, e.g., by the springs 652 and/or 752 in FIGS. 7 and 8 respectively. Moreover, the surface finish of the second section(s) 107 may substantially match that of the plurality of teeth 140 on the motive rollers 134.

In addition, the at least one first flexible section 106 may be comprised of a thinner, more flexible material than the second section(s) 107. In the illustrated embodiment, the flexible section(s) 106 either do not contact, or partially contact, the motive rollers 134. Thus, the flexible section(s) 106 may fold relatively easily and, as a result, take up less space when traveling between the support structure 128 and the housing structure 130 as illustrated and described above. The flexible section(s) 106 may also stretch to a greater diameter when circulating to the outside of the toroid's surface.

Further, the second section(s) 107 may have lower friction characteristics and be stiffer than the flexible material section(s) 106; such characteristics are well understood by those skilled in the art. This prevents the second section(s) 107 from bunching up while traveling between the support structure 128 and the housing structure 130. In another embodiment, the flexible material section(s) 106 may have higher friction characteristics to prevent the at least one first section material 106 from slipping against a surface of a body canal or cavity, section of pipe, lumen or other generally tubular space in which the toroid is traveling.

In some exemplary embodiments of an apparatus in accordance with the present invention, a frame is formed of a support structure and a series of at least two sets of interlocking rollers or skids located on the support structure. The support structure is located within the interior volume of the enclosed ring. The rollers or skids are located so as to maintain the flexible material of the enclosed ring between them. To further accommodate folds and wrinkles in the flexible material the rollers or skids may be suspended and may apply force to the flexible material and the matching rollers or skids. Embodiments of possible suspension mechanisms are illustrated in the Figures.

Figure 17:
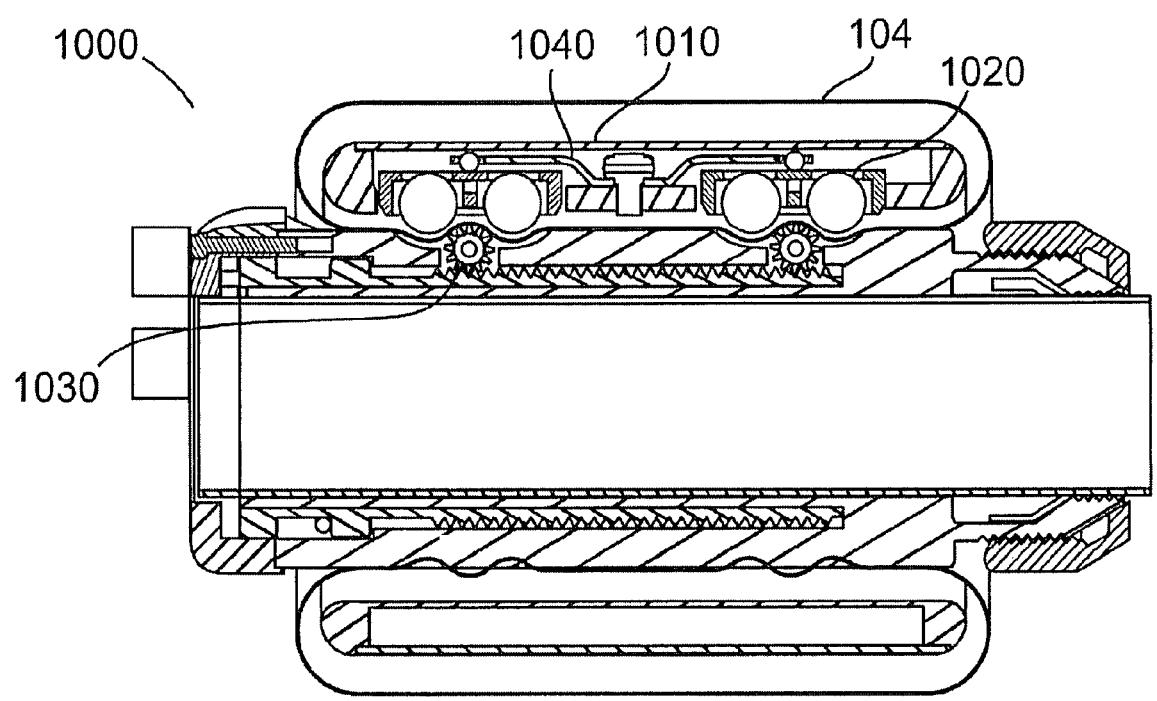
FIG. 17 provides an alternate embodiment of the endoscopic apparatus.

Turning now to FIG. 17, a cross section of one embodiment of the apparatus is illustrated. Apparatus 1000 comprises a support structure 1010 that rotatably supports a plurality of suspended motive rollers 1020. Thus, the bladder material 104 of the toroid as described and illustrated above is disposed between motive roller 1030 and suspended motive rollers 1020. The support structure 1010 is illustrated as housing a suspension mechanism 1040. Suspension mechanism 1040 supports a pair of suspended motive rollers 1020 on either end. Suspension mechanism 1040 allows the rollers to adjustably move vertically, laterally or rotationally to accommodate the environment in which the apparatus is traveling. Thus, the suspended motive rollers 1020 and/or skids as described above, may be suspended or held in place such that they may pivot in any direction so as to maintain the maximum contact surface area between the respective roller, toroid surface and matching interlocking rollers possible.

Figure 18A:
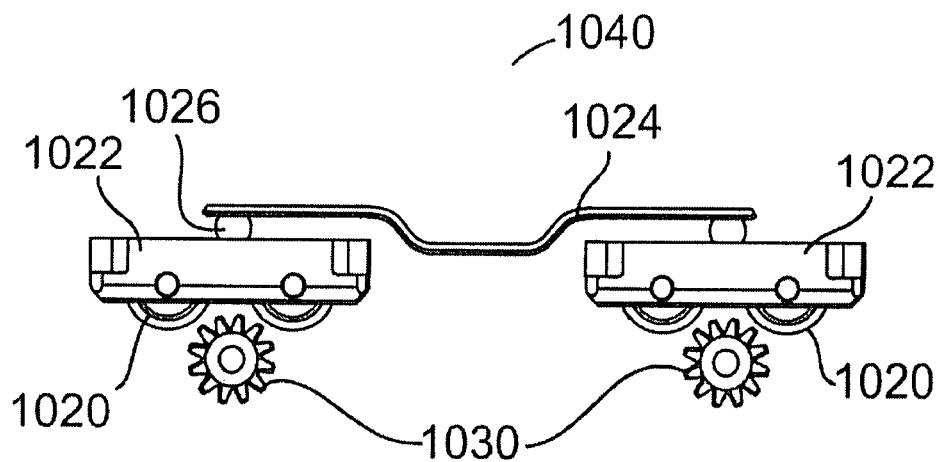
FIGS. 18A and 18B Illustrate side and top views, respectively, of one embodiment of a suspension mechanism.
Figure 18B:
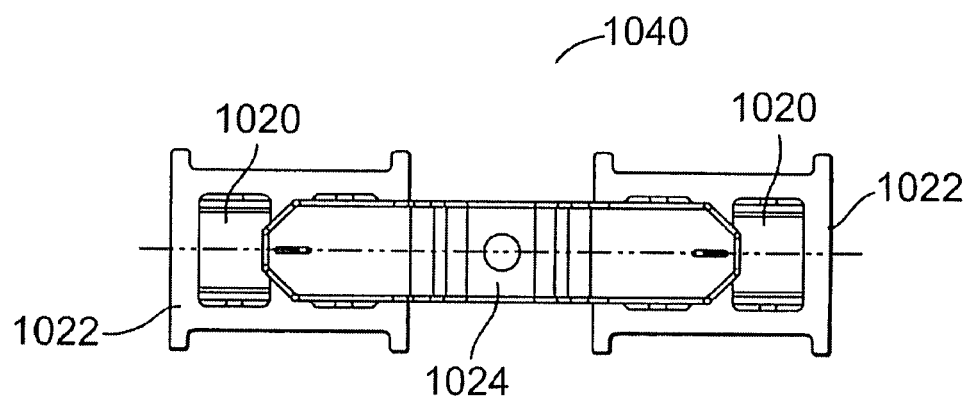

With reference now to FIGS. 18a and 18b, side and top views, respectively, of one particular embodiment of the suspension mechanism 1040 are provided. The bladder material 104 of the toroid is removed to facilitate illustration. Here, the suspended motive rollers 1020 are supported in a housing structure 1022 and interface with the interlocking motive rollers 1030 to cause the bladder material 104 of the toroid (not shown) to move. The suspension arm 1024 is rotatably engaged with the housing structure 1022 via a connective ball 1026 in an essentially gimbled fashion as well known to those in the art. The interface between the connective ball 1026 and the suspension arm 1024 allows pivoting of the suspended motive rollers 1020. The ball 1026 may be of a relatively flexible material in certain embodiments to allow additional flexibility and motion.

Figure 19A:
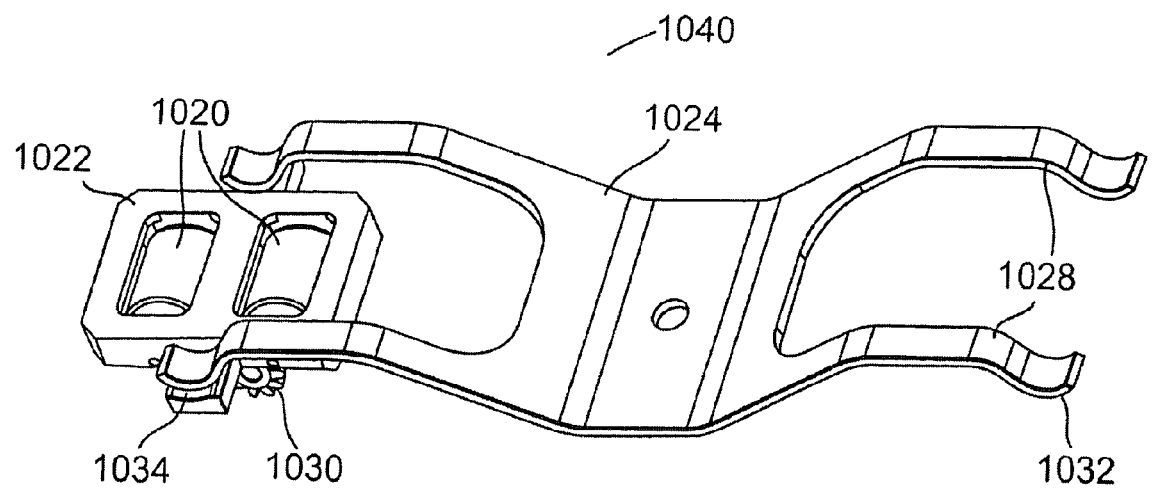
FIGS. 19A and 19B illustrate perspective and side views, respectively, of one embodiment of a suspension mechanism.
Figure 19B:
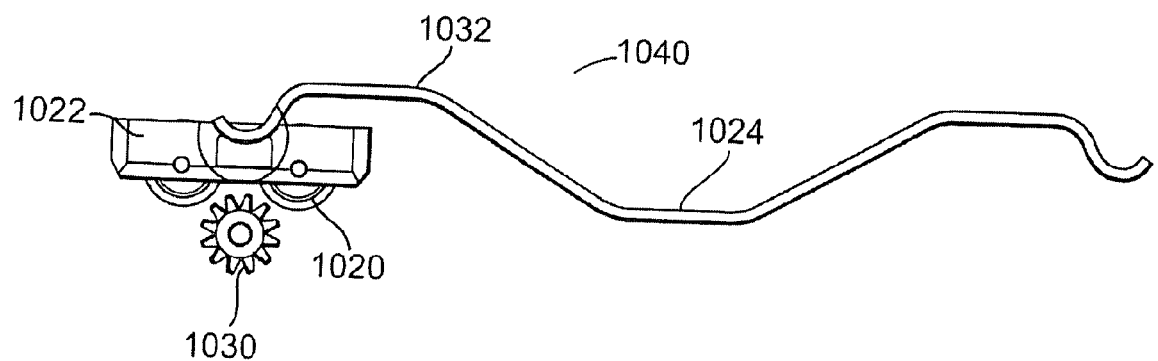

FIGS. 19A and 19B provide another embodiment of the suspension mechanism 1040. As above, the suspended motive rollers 1020 are supported in a housing structure 1022 and interface with the interlocking motive rollers 1030 to cause the bladder material 104 of the toroid (not shown) to move. Here, the suspension arm 1024 comprises arms 1028 with curved ends 1032 that are complementary to a curved receptacle 1034 located on the housing structure 1022. Such an arrangement allows the suspension arm 1024 the flexibility of vertical rotation as well as the ability to flex and/or pivot in virtually any direction to accommodate the environment in which the apparatus is traveling.

Figure 20A:
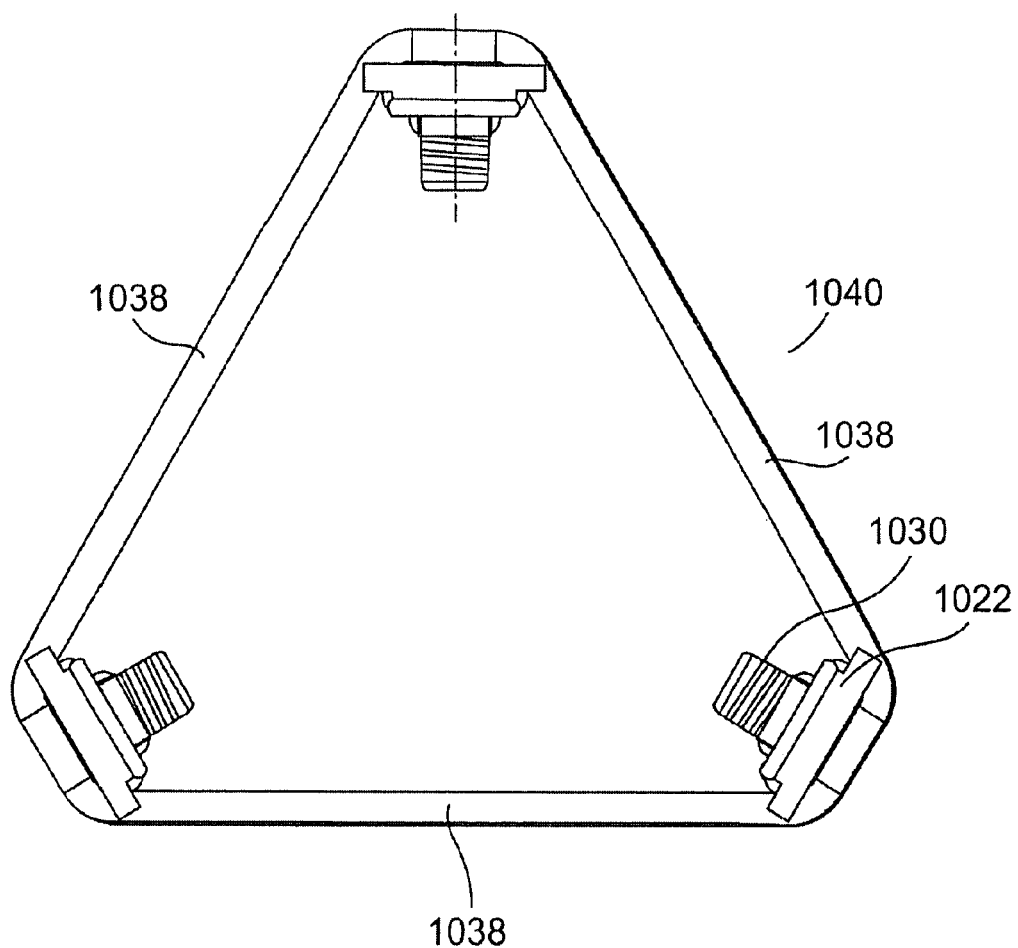
FIGS. 20A and 20B illustrate top and perspective views, respectively, of one embodiment of a suspension mechanism.
Figure 20B:
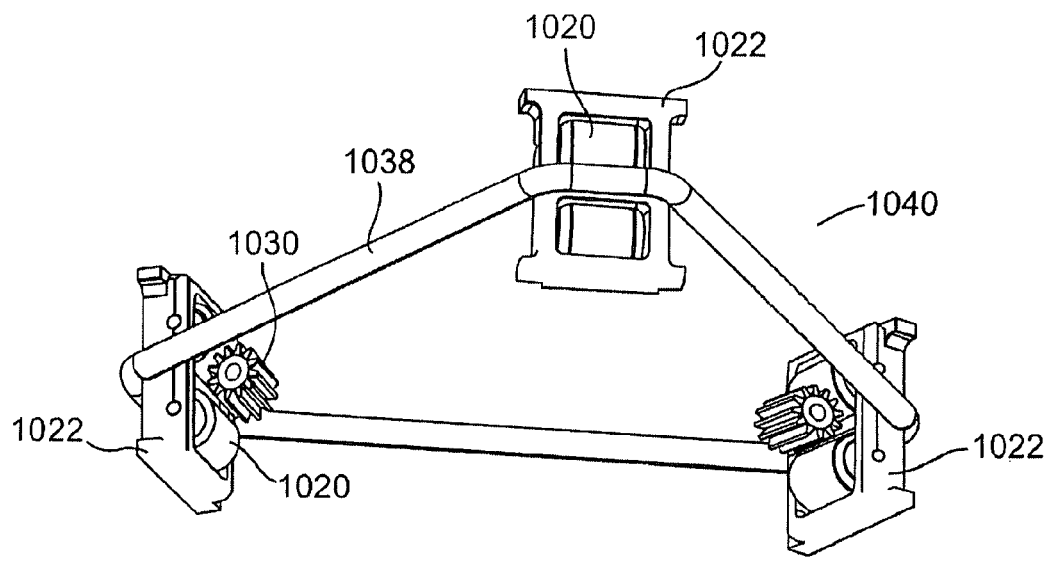

FIGS. 20A and 20B provide another embodiment of a suspension mechanism 1040. This embodiment provides at least two sets of interlocking rollers, three are shown for illustration purposes. The housing structure 1022, supports the suspended motive rollers 1020 and interface with the interlocking motive rollers 1030 to cause the bladder material 104 of the toroid (not shown) to move. In this embodiment, a flexible band 1038 is used to provide flexible support of the interlocking roller interface. Alternate embodiments include using coiled, leaf and/or torsion springs between the housing structures 1022.

The ends of support and housing structures may be tapered for some applications. Embodiments of the invention having tapered ends are well-suited, but not necessary for medical applications and procedures, e.g., colonoscopy or rectal examination. However, such tapering is not necessary for all applications, particularly those involving spaces or environments of large dimension. The tapered ends of the support and housing structures may serve a number of functions, including, but not limited to allowing the two structures to fit and work together without sliding apart; presenting a smooth and gradual surface to over which the flexible material travels, and easing the apparatus' through constrictions and its passage around curves and corners.

The series of at least two sets of interlocking rollers or skids are located on the support and housing structures or in the case where only a support structure is utilized, the rollers or skids are located on the support structure. A set of rollers or skids may be comprised of one or more roller, one or more skid or combination thereof located on one or more of the structures. A set may be formed of a single roller or skid, a pair of adjacent rollers or skid, a single roller or skid on one structure and a pair comprised of two or more rollers, two or more skids or a combination of both on the other, and other variations and combinations of rollers and skids located in corresponding aligned position on each structure. The rollers or skids are interlocked in two directions, along and across the apparatus' central axis. The interlocking is done in such a way as to maintain a generally constant or fixed distance between the support and housing structures, so that they are in a generally fixed spatial relationship. As shown in the figures, the flexible material of the enclosed ring passes between the rollers or skids. This helps to prevent the toroid's flexible material from being compressed between the two structures except where it interacts with the rollers or skids. When powered, the rollers engage the flexible material and provide a motive, directional force to the flexible material which allows the apparatus to move in a forward or backward direction. With the exterior surface of the enclosed ring contacting and conforming to the interior surface or surfaces of a generally tubular space or environment, the powering of the rollers moves the flexible material as illustrated in the figures. This movement of the flexible material provides the self-propulsion for the apparatus.

If unpowered, the rollers or skids provide a means of facilitating the motion of the flexible material between the support and housing structures, for example when the apparatus is initially being introduced. When propelled, preferably, only the rollers on the advancing side of the apparatus are powered. This will tend to keep the flexible material from wrinkling, kinking and bunching-up by pulling the flexible material through the toroid's central cavity instead of pushing it. However, the apparatus can be operated with the rearward roller (rearward relative the direction of motion) being powered or both forward and rearward rollers being powered.

The fluid-filled toroid is also well adapted to the numerous curves, corners and constrictions found in body cavities and lumens. As one part of the shape is squeezed or pushed the liquid or gas is displaced and accommodated by the flexibility of the bladder.

Moreover, using methods well known to those skilled in the art, the apparatus may be remotely controlled by an operator as it enters and travels the subject tubular space. Thus, the operator may adjust the speed of advancement and/or the direction of travel remotely. Alternatively, other embodiments of the apparatus may comprise the ability to pre-program a direction, length of travel, speed and/or destination prior to entry into the subject tubular space. This capability may comprise, e.g., GPS technology, well known to those skilled in the art, wherein the apparatus is directed to proceed within the subject tubular space to a precise GPS coordinates.

Various embodiments of the apparatus may comprise a radiopaque material or the like in the toroid's bladder 104 to facilitate external monitoring of movement through the subject tubular space. Such radiopaque material facilitates locating the apparatus during operation within a tubular space and reduces and/or eliminates the possibility that the apparatus is advanced or retracted to a position that may result in damage to the surface of the tubular space or other object. In this connection, the additional section(s) 107 and/or the flexible material section(s) 106 may comprise radiopaque material. Various embodiments of the radiopaque implementation will readily present themselves to those skilled in the art. For example, the entire outer surface of the toroid may be radiopaque, wherein radiopaque material may be embedded throughout or interspersed substantially through the surface. Alternatively, at least one of the additional section(s) 107 or at least one of the flexible material section(s) 106 may be radiopaque.

The mechanisms that may be used to move the toroid's surface, or passively move around itself in a continuous motion from inside its central cavity along its central axis to the outside where the surface travels in the opposite direction until it again rotates into the central cavity are well known in the art. While the toroid is illustrated herein as being driven by the traction of the drive gear against the toiroid surface with a principally mechanical drive, many other drive methods and mechanisms will readily present themselves to those skilled in the art. Exemplary mechanisms comprise geared mechanical systems, passive mechanical systems, magnetic systems, inductive driven flexible material, inductive driven fluid within the bladder, mechanical, electrical, or systems that repeatedly grab or squeeze and push or pull the bladder material.

Piezoelectric "inchworm" mechanisms are also known, wherein the toroid may be gripped by one piezoelectric drive, moved by another piezoelectric drive that is orthogonal to the first and clamped at the new location by a third piezoelectric device that is parallel to the first one. The first piezoelectric drive would then release the toroid and the orthogonal piezoelectric drive would return the first drive to its original location. The process then repeats, providing incremental motion of the toroid.

The toroid may be made from, or impregnated with, a conductive material and propelled by inducing electrical eddy currents in the toroid from two or more sets of stationary electrical windings suitably excited. Moreover, the toroid may be made from, or impregnated with, a magnetic material and propelled by interaction with suitable magnetic fields from stationary electrical windings. Similarly, the fluid within the toroid's bladder may contain elements, particles or structures that, when excited by suitable electric or magnetic fields, may propel the toroid.

The mechanisms may further include pneumatic, hydraulic, thermal or equivalent methods of supplying energy to the toroid.

All such mechanisms, and the equivalent thereof, are well within the scope of the invention.

The apparatus may include an accessory tube, such as a flexible tube, connected to the apparatus and leading outside the patient or other space into which it is introduced. For example, as the apparatus enters and travels within the patient, the tube remains connected and is pulled by the device. It can also be pushed or pulled as a means of moving the inside a patient or other space. The accessory tube can be a single pathway or conduit or may contain multiple pathways or conduits which can be used to insert a variety of accessory devices into the patient or to connect such devices to external support devices know to those skilled in the art, including but not limited to computers, analytical or diagnostic equipment or other electronic equipment appropriate to the given application.

Various types of accessory devices can be utilized with or mounted to the apparatus. Such accessory devices include, but are not limited to, endoscopes, cameras, fiber optic cables, electronic communication cables, lasers, surgical instruments, medical instruments, diagnostic instruments, instrumentation, sensors, stent catheters, fluid delivery devices, drug delivery devices, electronic devices, tools, sampling devices, assay devices, other accessory devices, and combinations thereof.

Figure 21:
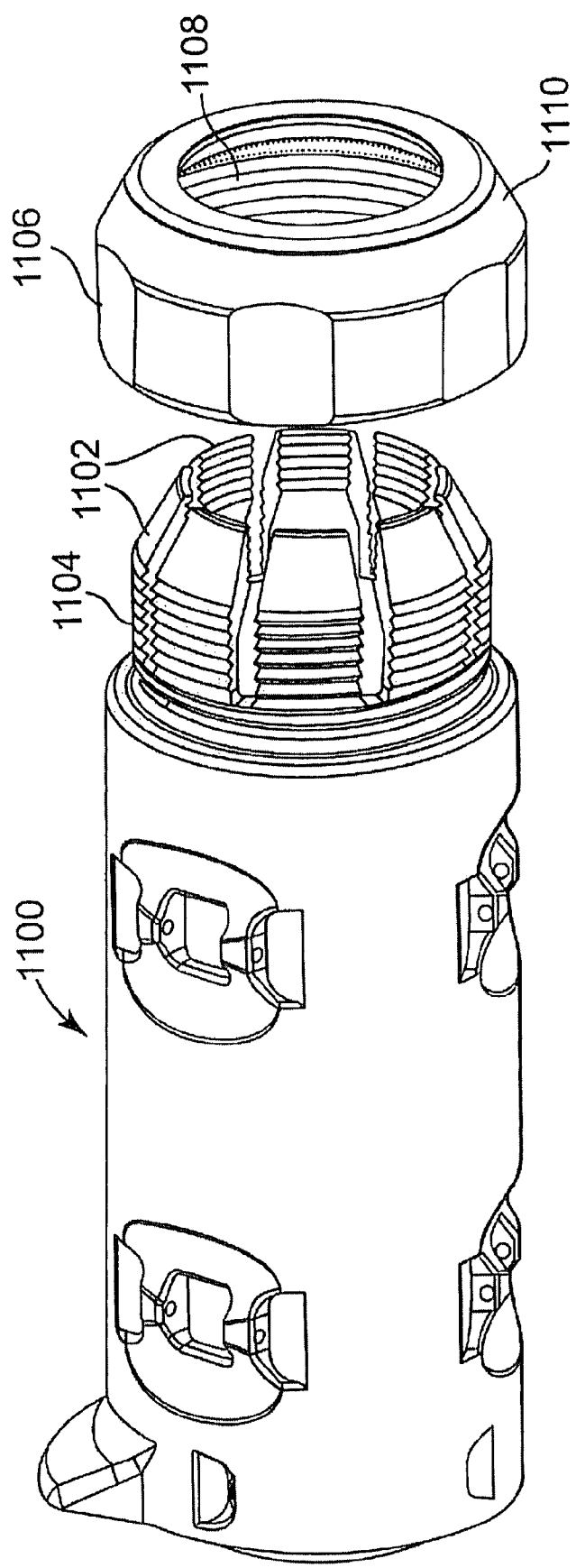
FIG. 21 provides a perspective view of one embodiment of the apparatus.

With reference to FIG. 21, the accessory device(s) may be attached to the apparatus using a flexible, multi-fingered collet 1100 or the equivalent. The collet fingers 1102 may be threaded 1104 on the outside to accept a clamping nut 1106 with a taper on the inside that presses the collet fingers 1102 directly against the accessory device (not shown) or through an intermediate device to minimize damage where the accessory device is delicate and fragile. The threaded side 1104 of the collet fingers 1102 may have a ramp. The nut 1106 may have a corresponding ramp on the inner thread surface 1108 so that the nut 1106 may be readily installed in the direction to tighten and clamp the apparatus to the accessory device but may not be removed without breaking off one or more of the collet fingers 1102. Moreover, the collet nut 1106 may have a tapered 1110 or otherwise similarly shaped exterior to ease the insertion of the accessory-carrying apparatus into lumens that are normally closed by muscular sphincter valves, e.g., the anus. Additional connection mechanisms may be readily apparent to those skilled in the art and are within the scope of the invention.

Figure 22:
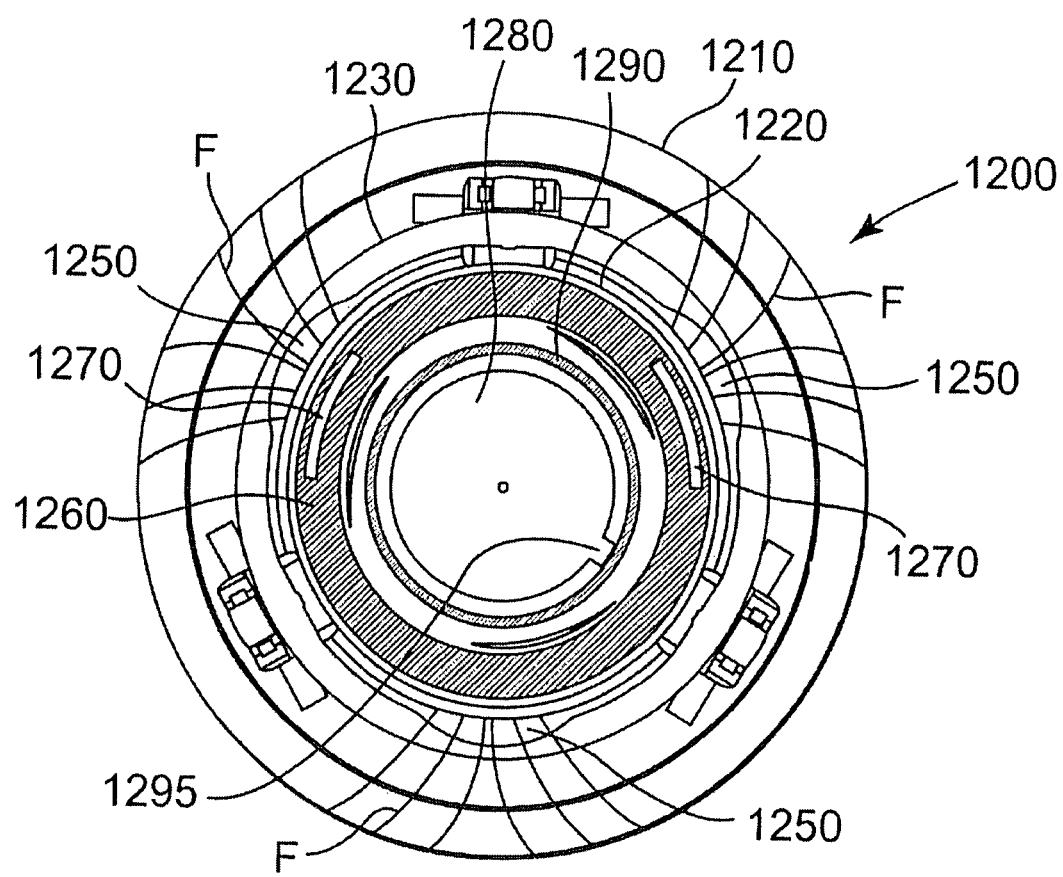
FIG. 22 provides a cutaway illustration of one embodiment of the apparatus.

Turning now to FIG. 22, one embodiment of the apparatus 1200 is illustrated in cutaway perspective. Thus, the toroid bladder outer surface 1210 and bladder inner surface 1220 are shown. An outer cylinder 1230 is provided within the space 1240 defined by the bladder outer surface 1210 and bladder inner surface 1220. A plurality of guides 1250 are provided on the outer cylinder and define enlarged regions. The guides 1250 function to facilitate guided folding or wrinkling of the toroid bladder material, particularly the flexible material sections as defined in connection with FIGS. 16A and 16B. The wrinkling and/or folding of the flexible material is indicated by lines marked with "F" in FIG. 22. Managing the wrinkling and folding of the toroidal bladder material facilitates motion of the apparatus through the tubular space as well as around corners, curves and obstructions.

FIG. 22 further illustrates an inner cylinder 1260, substantially concentric with the outer cylinder 1230. Along the longitudinal axis of the apparatus and the inner cylinder, fluid-flow channels 1270 are illustrated in the Figure. Such channels are useful when operating the apparatus in environments where continued fluid flow and maintaining fluid pressure are important; e.g., in an arterial space. The fluid flow channels 1270 function to allow the toroidal apparatus to fill the tubular space, while allowing the tubular space fluid to flow through the apparatus. In another embodiment, the fluid flow may be facilitated by providing an accessory device tube 1280 surrounded by an accessory device ring 1290 that, when tightened, clamps the accessory device within the toroidal apparatus. The accessory device ring 1290 is shown with a gap 1295. Fluid flow through the apparatus may be facilitated by allowing the gap 1295 to be sufficiently large so that when the accessory device is clamped within the accessory device ring 1290, the gap 1295 remains open.

Figure 23A:
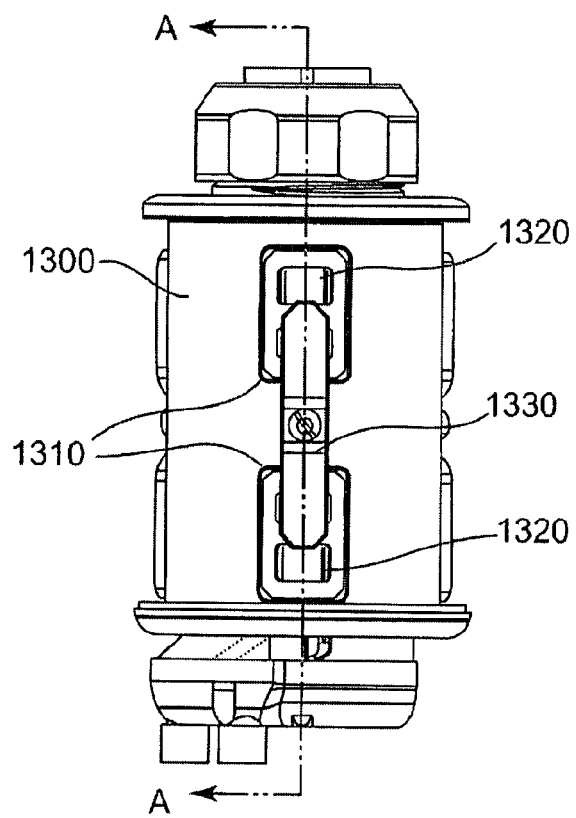
FIGS. 23A and 23B provide side and cutaway views, respectively, of an embodiment of the apparatus.
Figure 23B:
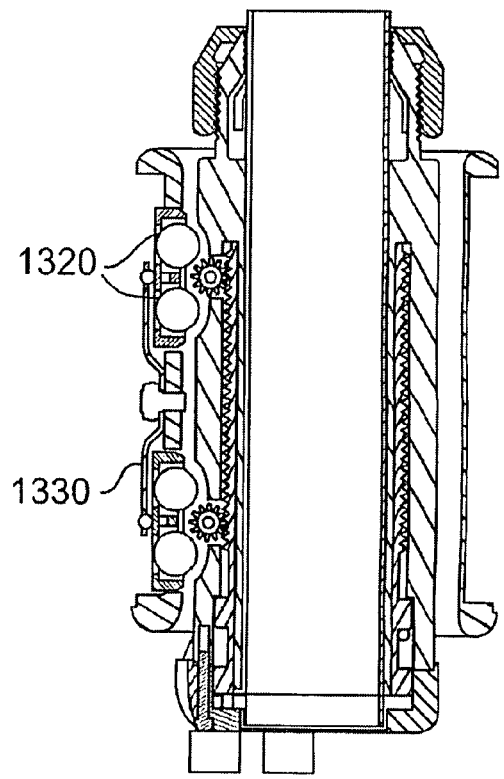

Turning now to FIGS. 23A and 23B, another embodiment of the inventive apparatus is provided. Here, there is provided an outer cylinder 1300, wherein a plurality of apertures 1310 are provided to engage the suspended motive rollers 1320, including when utilized, the suspension mechanism 1330 as described and illustrated above. The outer cylinder apertures 1310 are engaged by the suspension mechanism 1330 by any method well known to those skilled in the art. In this arrangement, the outer cylinder is located axially, angularly and radially by a combination of the suspended motive roller frames, embodied in this illustration by the suspension mechanism 1330.

Figure 24:
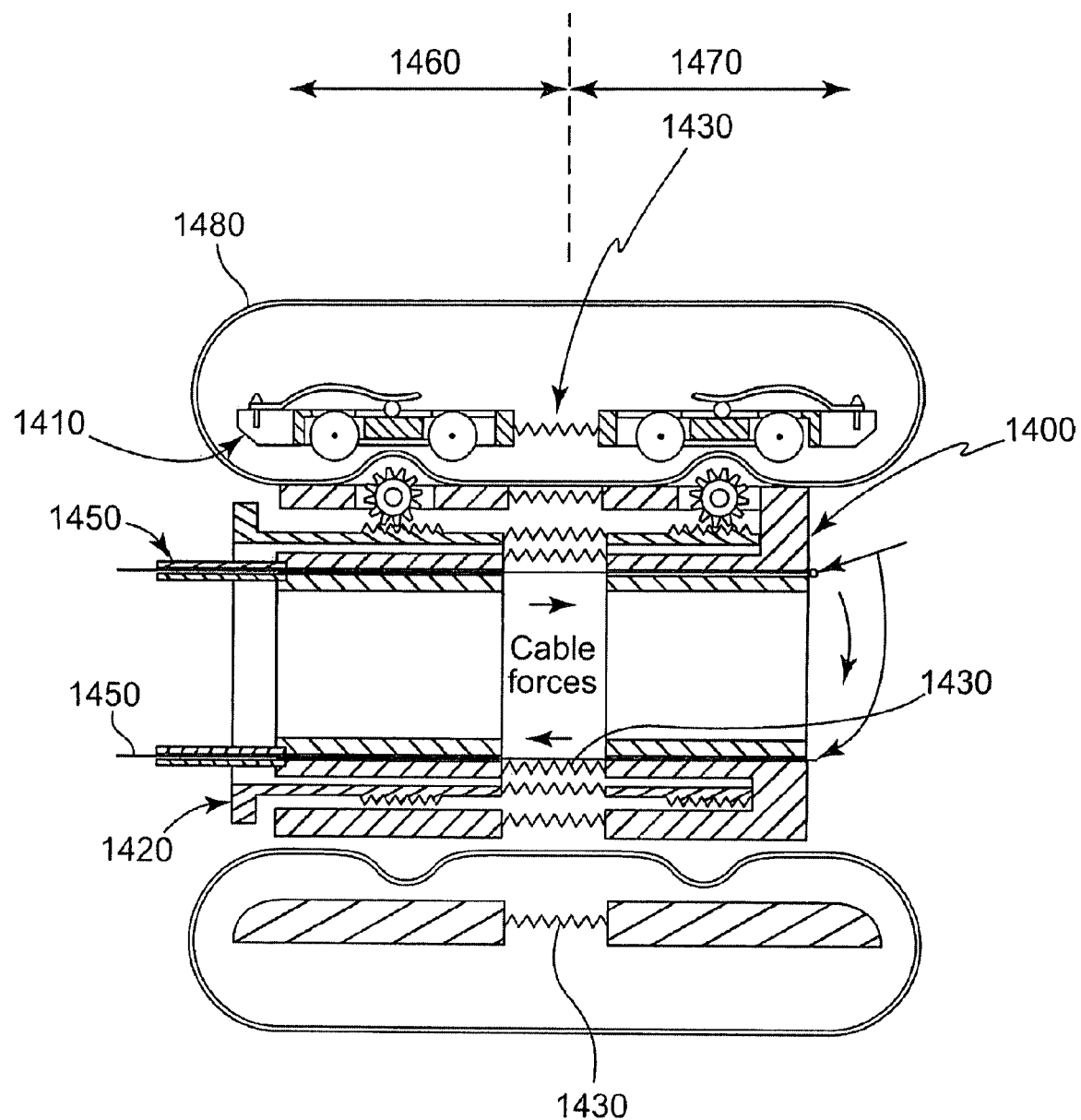
FIG. 24 is a cutaway view of one embodiment of the apparatus.

FIG. 24 illustrates an embodiment of the apparatus having an articulating frame. In this embodiment, the inner cylinder 1400 and outer cylinder 1410 need not be continuous rigid elements. The steerability and maneuverability of the apparatus may be improved by dividing the inner 1400 and outer 1410 cylinders and the worm gear 1420 into segments and connecting them with flexible couplings 1430, that may be torsionally rigid. A push-pull cable 1450 may be used to steer the front portion 1460 of the articulated apparatus with respect to the rear portion 1470. The toroidal bladder size 1480 may be changed by pushing or pulling on both cables 1450 simultaneously since the bladder comprises at least some flexible material. Other techniques for steering a self-propelled device may be obvious to those skilled in the art and are within the scope of the present invention.

Figure 25:
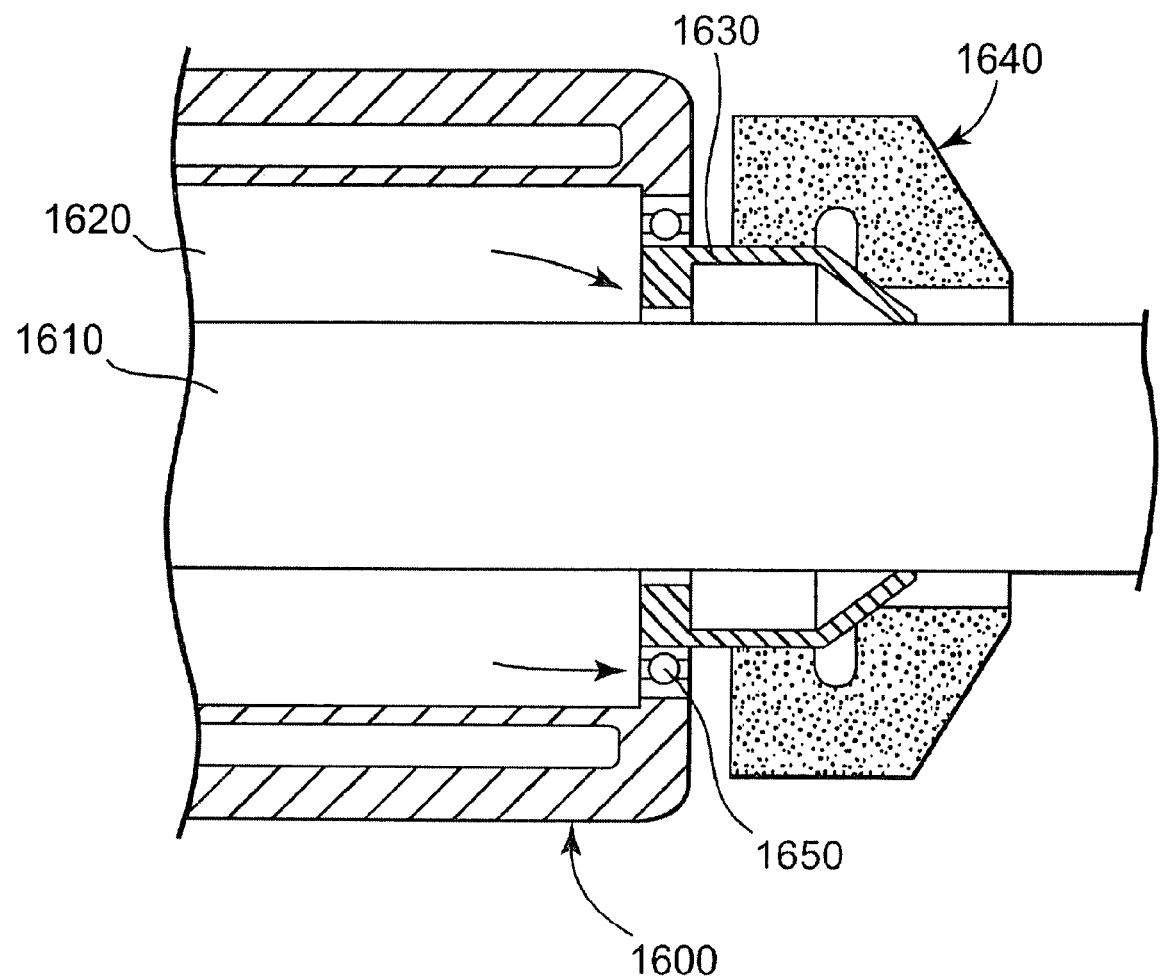
FIG. 25 is a partial cutaway view of one embodiment of the apparatus.

With reference now to FIG. 25, an accessory device swivel is provided. Generally, procedures performed with the self-propelled endoscopic device may require the accessory to be rotated about an axis parallel to the axis of travel (longitudinal axis generally), while the toroid may remain stationary. This rotation may be necessary to view a feature in the tubular space and/or lumen or bring a tool or other analytical accessory device requiring a specific operational orientation, into proper position for operation. In the illustrated embodiment, the apparatus inner cylinder 1600 is provided in cutaway view, with an accessory 1610 housed within the accessory device tube 1620 and held in place by a collet 1630, including a collet nut 1640. A swivel bearing 1650 is provided on the inner cylinder 1600. Such bearing 1650, facilitates the rotation of the accessory 1610 as described above. Other mechanisms to rotate the accessory 1610 will be readily apparent to those skilled in the art and are within the scope of the present invention.

The material requirements for the various components of the invention can be fulfilled by a number of substances. For medical applications, all materials must possess a high degree of biocompatibility and be capable of withstanding sterilization methods know to those skilled in the art, such as radiation, steam or chemical vapor.

The toroid may be fluid-filled or filled with gel or other relatively flexible material. The material comprising the bladder may be impermeable, thus retaining the fluid, gel or other material within the bladder while not allowing external materials to enter the impermeable bladder. Alternatively, the material may be permeable or semipermeable. In these embodiments, the bladder may be substantially empty or filled with a material of a certain osmotic pressure. Thus, when the toroidal endoscopic apparatus is placed into the target tubular environment, the bladder may, depending upon osmotic pressure gradients, fill with fluid from the environment. This embodiment may be useful when contamination of the target environment is of particular concern.

The fluid located inside the enclosed ring or bladder may be a liquid, such as a light oil, water, saline solution, lubricant; a gas, such as air, nitrogen, or carbon dioxide; or a combination thereof. Preferably, for medical or veterinary application or use, the fluid will be non-toxic. For the enclosed ring or bladder the flexible material should be a material with puncture, rupture and abrasion resistance characteristic as appropriate to the conditions of the interior surface of the space or environment into which the apparatus will be introduced. The flexible material may also possess a textured surface that would assist its motion against the surface of the lumen it traverses. Other characteristics to be considered in the selection of suitable materials, for example, softness, flexibility and conformability. The toroid's material must also be capable of being sealed into an enclosed ring or closed bladder by some means such as heat sealing, an adhesive or a chemical bond. A variety of polymeric or plastic materials can be used as the flexible material.

The support and housing structures may be formed of either a semi-flexible or semi-rigid material such as a polymer or a rigid material, such as stainless steel, a composite material or combinations thereof. The rollers or skids will require a material or group of materials that is high in strength and capable of being formed into very small parts. The roller material must also provide a sufficiently high degree of friction (not slip) against the flexible material without damaging it while the skids must provide a sufficiently low degree of friction (slip) against the flexible material without damaging it. The surfaces of the support and housing structures may be comprised of one or more materials that reduce or eliminate friction caused by the motion of the flexible material across the surfaces of the support and housing structures.

For applications of a non-medical nature, the materials required must retain most properties described above but do not necessarily require biocompatibility or sterilization tolerance. The materials used for the invention in non-medical applications will require sufficient durability and compatibility to suit the environment in which they are to be used.

The endoscopic toroidal device may be combined with other devices, either in parallel or in series. Thus, at least two toroidal devices may be used in combination, wherein each device carries a different complement of accessory device(s) and covers and different region of the tubular space. Moreover, the construction of such an assembly of devices need not be limited to a simple linear model.

The toroid size of the subject apparatus need not be fixed. The size of the toroid may, in certain embodiments, by changed by, e.g., breaking, puncturing or otherwise opening a small high pressure capsule placed in the toroid at the time of manufacture. This may cause the flexible material of the bladder of the toroid to expand. Similar effects may be achieved by initiating reversible or irreversible chemical reactions in the bladder fluid of the toroid. Such reactions may be initiated or reversed by thermal, chemical, electrical means.

Though a number of applications and uses of the apparatus of the invention have been identified herein above, additional applications and uses include, but are not limited to, inspection of difficult to reach pipes, tubes and caverns by carrying a camera or other optical, electrical or mechanical inspection device; transporting remotely controlled tools for use in difficult to reach locations; routing or pulling cable, wires rope, etc. through long narrow passages; pushing or pulling material through a pipe by taking advantage of the invention's ability to conform to the shape of its environment allowing it to provide a seal between the spaces on either side, i.e. the invention could facilitate emptying a pipe of material without mixing it with air or other material on the other side of the invention. Many of these applications would work equally well if the device was self-propelled or simply pushed or pulled from the outside.

While exemplary embodiments of this invention and methods of practicing the same have been illustrated and described, it should be understood that various changes, adaptations, and modifications might be made therein without departing from the spirit of the invention and the scope of the appended claims.

The invention claimed is:

1. An apparatus comprising:
a self-enclosed tube, sized and shaped to fit within and engage a cavity or lumen, of a living body, the tube comprising an inner surface revolving to define an enclosed region and an outer surface that revolves to turn outward to engage the cavity or lumen and to turn inward to encompass a central region defining a concentric longitudinal path;
an attachment, coupled to the tube, the attachment configured to carry an optical viewing apparatus; and
wherein the tube is powered to promote relative movement between the tube and the cavity or lumen, and to thereby facilitate carrying the optical viewing apparatus, with respect to the cavity or lumen, in at least one of a forward or reverse direction generally along the longitudinal path; and
wherein the tube comprises an everting toroidal shape that separates the enclosed region from the central region,
a mechanical power transmission, spinning around an axis that follows the longitudinal path to provide a spinning mechanical power; and
a directional power converter, coupled to the mechanical power transmission, the directional power converter configured to convert the spinning mechanical power to a linear impelling power that drives the tube in at least one of the forward or reverse direction along the longitudinal path;
wherein the self-enclosed tube is sized and shaped to fit within and engage a human or animal body cavity or lumen; and wherein the attachment is configured to be secured to a portion of the optical viewing apparatus,
wherein the directional power converter comprises a toothed roller wheel located outside the enclosed region, and
wherein the apparatus further comprises a mechanical bias element, located within the enclosed region, the mechanical bias element configured to contact an interior surface of the tube to bias an exterior surface of the tube against the toothed roller wheel so that the mechanical bias element and the toothed roller wheel bias an interior portion of the tube generally toward the longitudinal path.

2. The apparatus of claim 1, in which the enclosed region of the tube provides an impermeable chamber capable of carrying at least one of a fluid and a gas.

3. The apparatus of claim 1, wherein
the mechanical power transmission comprises an elongate member configured to transmit power from a proximal portion, configured to be located outside the cavity or lumen, to a more distal portion, configured to be located closer to the tube; and
the directional power converter is located at or near the more distal portion of the elongate member.

4. The apparatus of claim 3, wherein the directional power converter comprises a worm gear.

5. The apparatus of claim 3, wherein the directional power converter comprises a mechanical power coupling, and wherein the mechanical power coupling comprises an alternating sequence of peaks separated by respective grooves.

6. The apparatus of claim 1, comprising a rigid generally cylindrical first structure, located within the enclosed region.

7. The apparatus of claim 6, comprising a rigid generally cylindrical second structure, located within the central region; and
wherein the first and second structures are engagably mechanically coupled such that the tube is permitted to pass between the first and second structures.

8. The apparatus of claim 1, wherein at least a portion of an exterior portion of the tube is configured to engage the toothed roller wheel.

9. The apparatus of claim 8, wherein the portion of the exterior portion of the tube comprises teeth.

10. The apparatus of claim 1, wherein the attachment comprises a collet.

11. The apparatus of claim 1, comprising a groove, substantially parallel to a direction of a longitudinal access, the groove located against at least one of an interior or exterior portion of the tube, the groove configured to accommodate folding, wrinkling, or other size contracting of the tube.

12. The apparatus of claim 1, comprising an articulating frame, the frame configured to permit a first portion of the tube to articulate by deviating away from the concentric longitudinal path while a second portion of the tube, located across the central region from the first portion of the tube, articulates by deviating toward the longitudinal axis.

13. The apparatus of claim 12, comprising a remote actuator, controllable from outside of the cavity or lumen to actuate the articulation of the first and second portions of the tube.

14. The apparatus of claim 1, wherein the attachment is configured to secure the optical viewing apparatus at least partially located in the central region.

15. The apparatus of claim 1, in which the enclosed region of the tube provides a permeable or substantially permeable chamber.

16. The apparatus of claim 1, in which the enclosed region of the tube is substantially unfilled.

17. The apparatus of claim 7, wherein the second structure comprises at least one aperture configured to receive a portion of a mechanical bias element, located within the enclosed region and configured to bias an interior portion of the tube generally toward the longitudinal path, to thereby axially or radially lock the first structure relative to the second structure.

18. The apparatus of claim 1, in which the tube comprises at least a first section and a second section, the first section of the tube differing from the second section of the tube in at least one of thickness, stiffness, texture, surface finish, surface pattern, durometer, flexibility, durability, friction characteristics, color, hydrophilic or hydrophobic tendency, elasticity, a wear characteristic, permeability, melting point, biocompatibility, or solubility.

* * * * *